(12) United States Patent
Sherwood et al.

(10) Patent No.: US 11,835,435 B2
(45) Date of Patent: Dec. 5, 2023

(54) SYSTEMS AND METHODS FOR DETECTING A HEALTH CONDITION

(71) Applicant: REGENTS OF THE UNIVERSITY OF MINNESOTA, Minneapolis, MN (US)

(72) Inventors: Gregory J. Sherwood, North Oaks, MN (US); Justin Theodore Nelson, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 625 days.

(21) Appl. No.: 16/696,348

(22) Filed: Nov. 26, 2019

(65) Prior Publication Data
US 2020/0166435 A1 May 28, 2020

Related U.S. Application Data

(60) Provisional application No. 62/771,856, filed on Nov. 27, 2018.

(51) Int. Cl.
*G16H 50/20* (2018.01)
*G16H 50/30* (2018.01)
(Continued)

(52) U.S. Cl.
CPC ........... *G01N 1/2226* (2013.01); *G01N 27/22* (2013.01); *G16H 15/00* (2018.01); *G16H 20/00* (2018.01);
(Continued)

(58) Field of Classification Search
CPC ................ G01N 1/2226; G01N 27/22; G01N 2001/2229; G01N 2027/222; G01N 33/53;
(Continued)

(56) References Cited

U.S. PATENT DOCUMENTS 3,661,528 A 5/1972 Falk
3,952,730 A 4/1976 Key
(Continued)

FOREIGN PATENT DOCUMENTS

CN 102183557 9/2011
CN 102941042 2/2013
(Continued)

OTHER PUBLICATIONS

Bhadra et al. "Non-destructive detection of fish spoilage using a wireless basic volatile sensor", https://www.sciencedirect.com/science/article/pii/S0039914014010005 (Year: 2015).*
(Continued)

*Primary Examiner* — Mamon Obeid
*Assistant Examiner* — Alaaeldin M Elshaer
(74) *Attorney, Agent, or Firm* — Pauly, DeVries Smith & Deffner LLC

(57) ABSTRACT

Embodiments herein include a method for detecting a health condition of a subject. The method can include obtaining a biological sample from the subject and placing it into a container having a headspace surrounding the biological sample. The method can include contacting a gas from the headspace with a chemical sensor element, the chemical sensor element including one or more discrete graphene varactors. The method can include sensing and storing capacitance of the discrete graphene varactors to obtain a sample data set. Other embodiments are also included herein.

20 Claims, 14 Drawing Sheets

(51) Int. Cl.
*G01N 27/22* (2006.01)
*G01N 1/22* (2006.01)
*G16H 15/00* (2018.01)
*G16H 20/00* (2018.01)

(52) U.S. Cl.
CPC ............ *G16H 50/20* (2018.01); *G16H 50/30* (2018.01); *G01N 2001/2229* (2013.01); *G01N 2027/222* (2013.01)

(58) Field of Classification Search
CPC .... G01N 33/00; G01N 27/414; G01N 33/497; G16H 15/00; G16H 50/30; G16H 50/20; G16H 20/00
USPC .......................................... 705/2, 3; 436/151
See application file for complete search history.

(56) References Cited

U.S. PATENT DOCUMENTS

| | | |
|---|---|---|
| 3,981,297 A | 9/1976 | Dunn et al. |
| 4,820,011 A | 4/1989 | Umegaki et al. |
| 4,901,727 A | 2/1990 | Goodwin |
| 5,174,290 A | 12/1992 | Fiddian-Green |
| 5,186,172 A | 2/1993 | Fiddian-Green |
| 5,357,971 A | 10/1994 | Sheehan et al. |
| 5,423,320 A | 6/1995 | Salzman et al. |
| 5,704,368 A | 1/1998 | Asano et al. |
| 5,834,626 A | 11/1998 | De Castro et al. |
| 5,928,155 A | 7/1999 | Eggers et al. |
| 6,006,121 A | 12/1999 | Vantrappen et al. |
| 6,029,076 A | 2/2000 | Fiddian-Greene et al. |
| 6,085,576 A | 7/2000 | Sunshine et al. |
| 6,149,624 A | 11/2000 | McShane |
| 6,170,318 B1 | 1/2001 | Lewis |
| 6,192,168 B1 | 2/2001 | Feldstein et al. |
| 6,238,339 B1 | 5/2001 | Fiddian-Greene et al. |
| 6,248,078 B1 | 6/2001 | Risby et al. |
| 6,312,390 B1 | 11/2001 | Phillips et al. |
| 6,480,734 B1 | 11/2002 | Zhang et al. |
| 6,599,253 B1 | 7/2003 | Baum et al. |
| 6,615,066 B2 | 9/2003 | Huybrechts et al. |
| 6,712,770 B2 | 3/2004 | Lin et al. |
| 6,726,637 B2 | 4/2004 | Phillips et al. |
| 6,733,464 B2 | 5/2004 | Olbrich et al. |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B1 | 2/2007 | Turcott et al. |
| 7,426,848 B1 | 9/2008 | Li et al. |
| 7,459,312 B2 | 12/2008 | Chen et al. |
| 7,704,214 B2 | 4/2010 | Meixner et al. |
| 7,809,441 B2 | 10/2010 | Kane et al. |
| 7,871,572 B2 | 1/2011 | Yang et al. |
| 7,955,562 B2 | 6/2011 | Hong et al. |
| 7,972,277 B2 | 7/2011 | Oki et al. |
| 7,988,917 B2 | 8/2011 | Roesicke et al. |
| 7,992,422 B2 | 8/2011 | Leddy et al. |
| 8,043,860 B2 | 10/2011 | Leznoff et al. |
| 8,052,933 B2 | 11/2011 | Schirmer et al. |
| 8,080,206 B2 | 12/2011 | Leddy et al. |
| 8,124,419 B2 | 2/2012 | Grigorian et al. |
| 8,153,439 B2 | 4/2012 | Zamborini et al. |
| 8,154,093 B2 | 4/2012 | Passmore et al. |
| 8,157,730 B2 | 4/2012 | Tucker et al. |
| 8,222,041 B2 | 7/2012 | Pearton et al. |
| 8,244,355 B2 | 8/2012 | Bennett et al. |
| 8,294,135 B2 | 10/2012 | Lebedev et al. |
| 8,366,630 B2 | 2/2013 | Haick et al. |
| 8,479,731 B2 | 7/2013 | Heinonen et al. |
| 8,481,324 B2 | 7/2013 | Nakhoul et al. |
| 8,494,606 B2 | 7/2013 | Debreczeny et al. |
| 8,529,459 B2 | 9/2013 | Stahl, Jr. et al. |
| 8,581,262 B2 | 11/2013 | Pan et al. |
| 8,597,953 B2 | 12/2013 | Haick et al. |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Goldshtein et al. |
| 8,951,473 B2 | 2/2015 | Wang et al. |
| 8,955,367 B2 | 2/2015 | Gouma et al. |
| 8,961,830 B2 | 2/2015 | Reynolds et al. |
| 9,011,779 B1 | 4/2015 | Anglin, Jr. et al. |
| 9,029,168 B2 | 5/2015 | Mannoor et al. |
| 9,034,170 B2 | 5/2015 | Blackburn et al. |
| 9,085,715 B2 | 7/2015 | Berthelot et al. |
| 9,103,775 B2 | 8/2015 | Bradley et al. |
| 9,138,169 B2 | 9/2015 | Beard |
| 9,147,398 B2 | 9/2015 | White et al. |
| 9,147,851 B1 | 9/2015 | Bartsch et al. |
| 9,267,908 B2 | 2/2016 | Wang et al. |
| 9,299,238 B1 | 3/2016 | Ahmad et al. |
| 9,315,848 B2 | 4/2016 | Haick et al. |
| 9,316,637 B2 | 4/2016 | Ren et al. |
| 9,324,825 B2 | 4/2016 | Ravesi et al. |
| 9,366,664 B2 | 6/2016 | Anglin, Jr. et al. |
| 9,410,040 B2 | 8/2016 | Li et al. |
| 9,513,244 B2 | 12/2016 | Koester |
| 9,528,979 B2 | 12/2016 | Haick et al. |
| 9,618,476 B2 | 4/2017 | Goldsmith |
| 9,638,169 B2 | 5/2017 | Obrecht |
| 9,642,577 B1 | 5/2017 | Li et al. |
| 9,671,392 B2 | 6/2017 | Jeppsen et al. |
| 9,689,836 B2 | 6/2017 | Makaram et al. |
| 9,696,311 B2 | 7/2017 | Haick et al. |
| 9,763,600 B2 | 9/2017 | Van Kesteren et al. |
| 9,765,395 B2 | 9/2017 | Goldsmith |
| 9,775,241 B2 | 9/2017 | Walczak et al. |
| 9,859,034 B2 | 1/2018 | Sjong |
| 9,936,897 B2 | 4/2018 | Carlson et al. |
| 9,977,011 B2 | 5/2018 | Beck et al. |
| 10,034,621 B2 | 7/2018 | Wondka et al. |
| 10,046,323 B2 | 8/2018 | Bos |
| 10,307,080 B2 | 6/2019 | Ssenyange et al. |
| 10,493,276 B2 | 12/2019 | Moffitt et al. |
| 10,543,035 B2 | 1/2020 | Sutermeister et al. |
| 10,770,182 B2 | 9/2020 | Sherwood et al. |
| 10,852,264 B2 | 12/2020 | Kelly et al. |
| 11,079,371 B2 | 8/2021 | Zhen et al. |
| 11,085,921 B2 | 8/2021 | Livache et al. |
| 11,172,846 B2 | 11/2021 | Sherwood et al. |
| 11,191,457 B2 | 12/2021 | Sherwood et al. |
| 11,262,354 B2 | 3/2022 | Sherwood |
| 11,662,325 B2 | 5/2023 | Sherwood et al. |
| 11,714,058 B2 | 8/2023 | Kelly et al. |
| 2002/0123749 A1 | 9/2002 | Jain et al. |
| 2002/0142477 A1 | 10/2002 | Lewis et al. |
| 2003/0051733 A1 | 3/2003 | Kotmel et al. |
| 2004/0039295 A1 | 2/2004 | Olbrich et al. |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2007/0265509 A1 | 11/2007 | Burch et al. |
| 2008/0021339 A1 | 1/2008 | Gabriel et al. |
| 2008/0038154 A1 | 2/2008 | Longbottom et al. |
| 2008/0052122 A1 | 2/2008 | Iliff |
| 2008/0146890 A1 | 6/2008 | Leboeuf et al. |
| 2008/0161709 A1 | 7/2008 | Bradley |
| 2008/0183910 A1 | 7/2008 | Natoli et al. |
| 2008/0228098 A1 | 9/2008 | Popov et al. |
| 2008/0317636 A1 | 12/2008 | Brahim et al. |
| 2009/0054799 A1 | 2/2009 | Vrtis et al. |
| 2009/0104435 A1 | 4/2009 | Hutchison et al. |
| 2009/0112115 A1 | 4/2009 | Huang et al. |
| 2009/0230300 A1* | 9/2009 | Trevejo ............ C12Q 1/04 73/23.3 |
| 2010/0024533 A1 | 2/2010 | Kimura et al. |
| 2010/0056892 A1 | 3/2010 | Ben-Barak et al. |

(56) References Cited

U.S. PATENT DOCUMENTS

| | | |
|---|---|---|
| 2010/0085067 A1 | 4/2010 | Gabriel et al. |
| 2010/0116021 A1* | 5/2010 | O'Brien .................. G01N 21/51 |
| | | 73/23.37 |
| 2010/0137733 A1 | 6/2010 | Wang et al. |
| 2010/0147303 A1 | 6/2010 | Jafari et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0268479 A1 | 10/2010 | Potyrailo et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0059476 A1* | 3/2011 | Shin ........................ C12M 41/34 |
| | | 435/287.5 |
| 2011/0143962 A1 | 6/2011 | Chaubron et al. |
| 2011/0201956 A1 | 8/2011 | Alferness et al. |
| 2011/0269632 A1 | 11/2011 | Haick et al. |
| 2011/0283770 A1 | 11/2011 | Hok |
| 2012/0100636 A1 | 4/2012 | Johal et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0306802 A1 | 12/2012 | McCracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0224761 A1 | 8/2013 | Imberty et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0331723 A1 | 12/2013 | Hernandez-Silveira et al. |
| 2013/0334579 A1 | 12/2013 | Accardi et al. |
| 2014/0018691 A1 | 1/2014 | Mcneill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0122515 A1 | 5/2014 | Lee et al. |
| 2014/0145735 A1 | 5/2014 | Koester et al. |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0275854 A1 | 9/2014 | Venkatraman et al. |
| 2014/0276168 A1 | 9/2014 | Satya et al. |
| 2014/0294675 A1 | 10/2014 | Melker et al. |
| 2014/0318535 A1 | 10/2014 | Bullock et al. |
| 2014/0378790 A1 | 12/2014 | Cohen |
| 2015/0013429 A1 | 1/2015 | Atkin et al. |
| 2015/0031582 A1 | 1/2015 | Cai et al. |
| 2015/0038378 A1 | 2/2015 | Cheng et al. |
| 2015/0044710 A1 | 2/2015 | Dasgupta et al. |
| 2015/0064796 A1 | 3/2015 | Fu et al. |
| 2015/0065365 A1 | 3/2015 | Ahmad |
| 2015/0164373 A1 | 6/2015 | Davis et al. |
| 2015/0196251 A1 | 7/2015 | Outwater et al. |
| 2015/0250408 A1 | 9/2015 | Ssenyange et al. |
| 2015/0257676 A1 | 9/2015 | Fries |
| 2015/0265184 A1 | 9/2015 | Wondka et al. |
| 2015/0289782 A1 | 10/2015 | Peverall et al. |
| 2015/0295562 A1 | 10/2015 | Agarwal et al. |
| 2015/0298115 A1 | 10/2015 | Campidelli et al. |
| 2015/0301021 A1 | 10/2015 | Haick et al. |
| 2015/0307936 A1* | 10/2015 | Goldsmith ......... G01N 27/4145 |
| | | 506/38 |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1* | 11/2015 | Anglin, Jr. ........... G01N 27/227 |
| | | 73/23.3 |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0093806 A1 | 3/2016 | Turchanin |
| 2016/0109440 A1 | 4/2016 | Sherwood et al. |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0289769 A1 | 10/2016 | Schwartz et al. |
| 2016/0334381 A1 | 11/2016 | King-smith et al. |
| 2016/0334386 A1 | 11/2016 | Anglin et al. |
| 2016/0356741 A1 | 12/2016 | Makaram et al. |
| 2016/0370337 A1 | 12/2016 | Blackley |
| 2017/0014043 A1 | 1/2017 | McDonnell |
| 2017/0042435 A1 | 2/2017 | Vermeulen et al. |
| 2017/0053068 A1 | 2/2017 | Pillai et al. |
| 2017/0067888 A1* | 3/2017 | Taslim ............. G01N 33/54366 |
| 2017/0082566 A1 | 3/2017 | Koester |
| 2017/0212116 A1 | 7/2017 | Braga et al. |
| 2017/0227491 A1* | 8/2017 | Johnson ............... H01L 51/0045 |
| 2017/0248541 A1 | 8/2017 | Liu |
| 2017/0307562 A1 | 10/2017 | Goldsmith |
| 2017/0307576 A1 | 10/2017 | Anglin, Jr. et al. |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0035932 A1 | 2/2018 | Massova |
| 2018/0037952 A1 | 2/2018 | Goldsmith |
| 2018/0037985 A1 | 2/2018 | Myers et al. |
| 2018/0110444 A1 | 4/2018 | Sherwood et al. |
| 2018/0328841 A1 | 11/2018 | Graham et al. |
| 2018/0336970 A1* | 11/2018 | Sherwood ............... A61B 5/082 |
| 2019/0025237 A1 | 1/2019 | Kelly et al. |
| 2019/0178837 A1 | 6/2019 | Xu et al. |
| 2019/0254538 A1 | 8/2019 | Erdman et al. |
| 2019/0257825 A1 | 8/2019 | Zhen et al. |
| 2019/0286866 A1 | 9/2019 | Gurt |
| 2019/0331661 A1 | 10/2019 | Zhen et al. |
| 2020/0191737 A1 | 6/2020 | Sherwood et al. |
| 2021/0057526 A1 | 2/2021 | Zhen et al. |
| 2021/0072208 A1 | 3/2021 | Sherwood et al. |
| 2021/0148848 A1 | 5/2021 | Kelly et al. |
| 2021/0341409 A1 | 11/2021 | Rognrud et al. |
| 2022/0334075 A1 | 10/2022 | Koester et al. |

FOREIGN PATENT DOCUMENTS

| | | |
|---|---|---|
| CN | 103332678 | 10/2013 |
| CN | 103950920 | 7/2014 |
| CN | 104914138 | 9/2015 |
| CN | 103852505 | 11/2015 |
| CN | 103877574 | 1/2016 |
| CN | 105445335 | 3/2016 |
| CN | 105527321 | 4/2016 |
| CN | 105688995 | 6/2016 |
| CN | 106152924 | 11/2016 |
| CN | 107180706 | 9/2017 |
| EP | 1764153 | 3/2007 |
| EP | 1806414 | 7/2007 |
| EP | 3093653 | 11/2016 |
| EP | 3431977 | 1/2019 |

(56) References Cited

FOREIGN PATENT DOCUMENTS

| | | |
|---|---|---|
| IN | 201627028955 | 10/2016 |
| JP | H11174051 | 7/1999 |
| JP | 2009244074 | 10/2009 |
| JP | 2011102747 | 5/2011 |
| JP | 2012122814 | 6/2012 |
| JP | 2016022415 | 2/2016 |
| JP | 2016122249 | 7/2016 |
| JP | 2017123912 | 7/2017 |
| KR | 20170057001 | 5/2017 |
| KR | 101797737 | 11/2017 |
| WO | 9325142 | 12/1993 |
| WO | 9947905 | 9/1999 |
| WO | 2001070114 | 9/2001 |
| WO | 2008088780 | 7/2008 |
| WO | 2009135070 | 11/2009 |
| WO | 2011109736 | 9/2011 |
| WO | 2012127213 | 9/2012 |
| WO | 2012135565 | 10/2012 |
| WO | 2012145247 | 10/2012 |
| WO | 2013095730 | 6/2013 |
| WO | 2013189502 | 12/2013 |
| WO | 2014064740 | 5/2014 |
| WO | 2015179623 | 11/2015 |
| WO | 2015191558 | 12/2015 |
| WO | 2016063148 | 4/2016 |
| WO | 2016064740 | 4/2016 |
| WO | 2016105464 | 6/2016 |
| WO | 2016145300 | 9/2016 |
| WO | 2017066583 | 4/2017 |
| WO | 2017095922 | 6/2017 |
| WO | 2017218464 | 12/2017 |
| WO | 2018075731 | 4/2018 |
| WO | 2018213564 | 11/2018 |
| WO | 2020102880 | 5/2020 |

OTHER PUBLICATIONS

Huang et al. "LC Passive Wireless Sensors Toward a Wireless Sensing Platform: Status, Prospects, and Challenges", https://ieeexplore.ieee.org/abstract/document/7558121 (Year: 2016).*
Zhang et al. "Capacitive Sensing of Glucose in Electrolytes Using Graphene Quantum Capacitance Varactors", https://pubs.acs.org/doi/full/10.1021/acsami.7b14864 (Year: 2017).*
Notice of Allowance for U.S. Appl. No. 16/037,218 dated Jul. 31, 2020 (20 pages).
Response to Communication Pursuant to Rules 161(1) and 162 EPC for European Patent Application No. 18731579.1 filed Jul. 17, 2020 (19 pages).
Response to Final Rejection dated Jun. 8, 2020 and Advisory Action dated Sep. 4, 2020, for U.S. Appl. No. 15/621,103, submitted via EFS-Web on Oct. 8, 2020, 16 pages.
Response to Final Rejection dated Jun. 8, 2020 for U.S. Appl. No. 15/621,103, submitted via EFS-Web on Aug. 20, 2020, 16 pages.
Response to Non-Final Rejection dated Jun. 29, 2020 for U.S. Appl. No. 15/787,985, submitted via EFS-Web on Sep. 29, 2020, 9 pages.
1Final Office Action for U.S. Appl. No. 15/621,103 dated Jun. 8, 2020 (21 pages).
Non-Final Office Action for U.S. Appl. No. 15/787,985 dated Jun. 29, 2020 (14 pages).
Office Action for Japanese Patent Application No. 2019-520955 dated Jul. 14, 2020 (5 pages) No English Translation.
Response to Final Rejection dated May 1, 2020 for U.S. Appl. No. 14/883,895, submitted via EFS-Web on Jul. 15, 2020, 12 pages.
Response to Non-Final Rejection dated Apr. 29, 2020 for U.S. Appl. No. 16/037,218, submitted via EFS-Web on Jul. 15, 2020, 7 pages.
Response to Non-Final Rejection dated Feb. 21, 2020 for U.S. Appl. No. 15/621,103, submitted via EFS-Web on May 20, 2020.
Arasaradnam, R. P. et al., "Review Article: Next Generation Diagnostic Modalities in Gastroenterology—Gas Phase Volatile compound biomarker detection," Alimentary Pharmacology and Therapeutics 2014; 39: 780-789 (10 pages).

Bhadra, Sharmista et al., "Non-destructive detection of fish spoilage using a wireless basic volatile sensor," Talanta, vol. 134, Dec. 25, 2014 pp. 718-723 (6 pages).
Boots, Agnes W. et al., "The Versatile Use of Exhaled Volatile Organic Compounds in Human Health and Disease," J. Breath Res. 6 (2012) 027108 (21 pages).
Chamberlain II, Richard V. et al., "Electrostatically-induced Inclusion of Anions in Cyclodextrin Monolayers on Electrodes," Langmuir 2000, 1388-1396 (9 pages).
"Communication Pursuant to Article 94(3) EPC," for European Patent Application No. 15790739.5 dated Dec. 17, 2019 (5 pages).
"Communication Pursuant to Article 94(3) EPC," for European Patent Application No. 18180455.0 dated Dec. 20, 2019 (3 pages).
"Communication Pursuant to Article 94(3) EPC," for European Patent Application No. 18180455.0 dated Feb. 11, 2019 (6 pages).
"Communication Pursuant to Article 94(3) EPC," for European Patent Application No. 18180455.0 dated Jul. 15, 2019 (5 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Di Natale, Corrado et al., "Lung Cancer Identification by the Analysis of Breath by Means of an Array of Non-Selective Gas Sensors," Biosensors and Bioelectronics 18 (2003) 1209-1218 (10 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
Ebrish, M. A. et al., "Operation of Multi-Finger Graphene Quantum Capacitance Varactors using Planarized Local Bottom Gate Electrodes," Applied Physics Letters, vol. 100, No. 14, Apr. 2012 (4 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
"European Search Report," for Dutch Patent Application No. 2019492 dated Apr. 12, 2018 (10 pages).
"European Search Report," for European Patent Application No. 18180455.0 dated Dec. 3, 2018 (5 pages).
"FDC1004 4-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments Aug. 2014—Revised Oct. 2016 (46 pages).
"File History," for U.S. Appl. No. 14/883,895 retrieved May 14, 2020 (301 pages).
"Final Office Action," for U.S. Appl. No. 15/787,985 dated Jan. 17, 2020 (16 pages).
"First Office Action," for Chinese Patent Application No. 201580056417.2 dated Feb. 11, 2019 (13 pages) with English summary.
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews, 2012, 14:112(11), pp. 6156-6214.
Georgakilas, Vasilios et al., "Noncovalent Functionalization of Graphene and Graphene Oxide for Energy Materials, Biosensing, Catalytic, and Biomedical Applications," Chem. Rev. 2016, 116, 5464-5519 (56 pages).
Guo, Yujing et al., "Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Report on Patentability," for PCT Application No. PCT/US2015/056243 dated May 4, 2017 (8 pages).

(56) References Cited

OTHER PUBLICATIONS

"International Preliminary Report on Patentability," for PCT Application No. PCT/US2017/057318 dated May 2, 2019 (11 pages).
"International Preliminary Report on Patentability," for PCT Application No. PCT/US2018/033166 dated Nov. 28, 2019 (8 pages).
"International Preliminary Report on Patentability," for PCT Application No. PCT/US2018/037144 dated Dec. 27, 2018 (7 pages).
"International Search Report and Written Opinion," for PCT Application No. PCT/US2015/056243, dated Jan. 26, 2016 (12 pages).
"International Search Report and Written Opinion," for PCT Application No. PCT/US2017/037144 dated Oct. 6, 2017 (11 pages).
"International Search Report and Written Opinion," for PCT Application No. PCT/US2017/057318 dated Feb. 6, 2018 (14 pages).
"International Search Report and Written Opinion," for PCT Application No. PCT/US2018/033166 dated Oct. 2, 2018 (12 pages).
"International Search Report and Written Opinion," for PCT Application No. PCT/US2019/063324 dated Mar. 27, 2020 (17 pages).
"International Search Report and Written Opinion," for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Li, Xiao et al., "Digital Health: Tracking Physiomes and Activity Using Wearable Biosensors Reveals Useful Health-Related Information," PLoS Biology 15.1 (2017): e2001402 (30 pages).
Ma, Rui et al., "Acetone Sensing Using Graphene Quantum Capacitance Varactors," 2016 IEEE Sensors, Orlando, FL, 2016 (3 pages).
Machado, Roberto F. et al., "Detection of Lung Cancer by Sensor Array Analyses of Exhaled Breath," Am J Respir Crit Care Med, vol. 171, 1286-1291 (2005), 6 pages.
"Mechanical Data," DGS (S-PDSO-G10) DSC0010B Package Outline, Example Board Layout, and Stencil Design. Texas Instruments 2016 (5 pages).
Nakhleh, Morad K. et al., "Diagnosis and Classification of 17 Diseases from 1404 Subjects via Pattern Analysis of Exhaled Molecules," ACS Nano 2017, 11, 112-125 (14 pages).
"Nano Mobile Healthcare Inc.," Company Profile on Reuters.com URL <http://www.reuters.com/finance/stocks/companyProfile?symbol=VNTH.PK> accessed Mar. 17, 2017 (2 pages).
Navaneethan, Udayakumar et al., "Volatile Organic Compounds in Bile Can Diagnose Malignant Biliary Strictures in the Setting of Pancreatic Cancer: A Preliminary Observation," Gastroinest Endosc. Dec. 2014;80(6):1038-45 (8 pages).
"Non-Final Office Action," for U.S. Appl. No. 15/621,103 dated Feb. 21, 2020 (58 pages).
"Non-Final Office Action," for U.S. Appl. No. 15/787,985 dated Oct. 10, 2019 (40 pages).
"Non-Final Office Action," for U.S. Appl. No. 15/982,506 dated Dec. 11, 2019 (41 pages).
"Non-Final Office Action," for U.S. Appl. No. 16/037,218 dated Apr. 29, 2020 (46 pages).
"Notice of Allowance," for U.S. Appl. No. 15/982,506 dated May 7, 2020 (17 pages).
"Office Action," for Japanese Patent Application No. 2019-517196 dated Feb. 4, 2020 (10 pages) with English Translation.
Olson, Eric J. et al., "Capacitive Sensing of Intercalated H2O Molecules Using Graphene," ACS Appl. Mater. Interfaces 2015, 7(46), 25804-25812 (29 pages).
Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
Putta, Chandrababu et al., "Palladium Nanoparticles on Beta-Cyclodextrin Functionalised Graphene Nanosheets: a Supramolecular Based Heterogeneous Catalyst for C-C Coupling Reactions under Green Reaction Conditions," RSC Adv., 2015, 5, 6652-6660 (9 pages).
"Response to Communication Pursuant to Article 94(3) EPC," for European Patent Application No. 15790739.5 filed Apr. 24, 2020 (16 pages).
"Response to Communication Pursuant to Article 94(3) EPC," for European Patent Application No. 18180455.0 filed Apr. 21, 2020 (24 pages).
"Response to Communication Pursuant to Article 94(3) EPC," for European Patent Application No. 18180455.0 filed Jun. 6, 2019 (44 pages).
"Response to Communication Pursuant to Article 94(3) EPC," for European Patent Application No. 18180455.0 filed Nov. 12, 2019 (9 pages).
"Response to Communication Pursuant to Rules 161(1) and 162 EPC," for European Patent Application No. 15790739.5 filed with the EPO Dec. 8, 2017 (14 pages).
"Response to Communication Pursuant to Rules 161(1) and 162 EPC," for European Patent Application No. 17733246.7 filed May 29, 2019 (22 pages).
"Response to Communication Pursuant to Rules 161(1) and 162 EPC," for European Patent Application No. 17794832.0 filed Dec. 6, 2019 (9 pages).
"Response to Final Rejection," dated Jan. 17, 2020 for U.S. Appl. No. 15/787,985, submitted via EFS-Web on Apr. 9, 2020, 12 pages.
"Response to Non-Final Rejection," dated Dec. 11, 2019 for U.S. Appl. No. 15/982,506, submitted via EFS-Web on Feb. 25, 2020, 13 pages.
"Response to Non-Final Rejection," dated Oct. 10, 2019 for U.S. Appl. No. 15/787,985, submitted via EFS-Web on Jan. 7, 2020, 17 pages.
Rojas, Maria T. et al., "Supported Monolayers Containing Preformed Binding-Sites—Synthesis and Interfacial Binding-Properties of a Thiolated Beta-Cyclodextrin Derivative," J. Am. Chem. Soc. 1995, 117, 336-343 (8 pages).
"Standard Terms and Conditions for Evaluation Modules," Texas Instruments 2016 (5 pages).
Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).
Wang, David "FDC1004: Basics of Capacitive Sensing and Applications," Application Report SNOA927, Texas Instruments Dec. 2014 (12 pages).
Wayu, Mulugeta B. et al., "Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).
Zhang, Yao et al., "Capacitive Sensing of Glucose in Electrolytes using Graphene Quantum Capacitance Varactors," ACS Appl. Mater. Interfaces 2017, 9, 38863-38869 (7 pages).
Zhang, Yao et al., "Glucose Sensing with Graphene Varactors," IEEE Sensors, Sensors 2016—Proceedings, Orlando, FL 2016 (3 pages).
Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
"Communication Pursuant to Article 94(3) EPC," for European Patent Application No. 17733246.7 dated Jan. 28, 2022 (6 pages).
"Communication Pursuant to Article 94(3) EPC," for European Patent Application No. 17794832.0 dated Mar. 7, 2022 (9 pages).
"First Office Action," for Chinese Patent Application No. 201810782878.3 dated Feb. 9, 2022 (14 pages) with English Summary.
"Office Action," for Japanese Patent Application No. 2018-133996 dated Jan. 25, 2022 (7 pages) with English Translation.
"Extended European Search Report," for European Patent Application No. 20214733.6 dated Apr. 21, 2021 (11 pages).

(56) References Cited

OTHER PUBLICATIONS

"Final Office Action," for U.S. Appl. No. 15/621,103 dated Apr. 22, 2021 (20 pages).
"Non-Final Office Action," for U.S. Appl. No. 14/883,895 dated May 20, 2021 (34 pages).
"Non-Final Office Action," for U.S. Appl. No. 15/787,985 dated Apr. 16, 2021 (16 pages).
Zhang, Xu et al., "A Wide Measurement Range and Fast Update Rate Integrated Interface for Capacitive Sensors Array," IEEE Transactions on Circuits and Systems—1: Regular Papers, Vo. 61, No. 1, Jan. 2014, pp. 2-11 (10 pages).
"International Preliminary Report on Patentability," for PCT Application No. PCT/US2019/063324 dated Jun. 10, 2021 (10 pages).
"Office Action," for Chinese Patent Application No. 201780065376.2 dated Apr. 27, 2021 (10 pages) with English Summary.
"Response to Final Rejection," dated Apr. 22, 2021 for U.S. Appl. No. 15/621,103, submitted via EFS-Web on Jun. 22, 2021, 13 pages.
"Response to Non-Final Rejection," dated Apr. 16, 2021 for U.S. Appl. No. 15/787,985, submitted via EFS-Web on Jun. 22, 2021, 11 pages.
"Second Office Action," for Chinese Patent Application No. 201780030595.7 dated Jun. 17, 2021 (8 pages) with English Summary.
"Office Action," for Japanese Patent Application No. 2019-520955 dated Feb. 9, 2021 (11 pages) with English Translation.
"Response to Communication Pursuant to Article 94(3) EPC," for European Patent Application No. 18731579.1 filed Mar. 15, 2021 (12 pages).
"Response to Final Rejection," dated Oct. 21, 2020 for U.S. Appl. No. 15/787,985, submitted via EFS-Web on Jan. 21, 2021, 8 pages.
"Response to Non-Final Rejection," dated Oct. 23, 2020 for U.S. Appl. No. 15/621,103, submitted via EFS-Web on Jan. 22, 2021, 17 pages.
"First Office Action," for Chinese Patent Application No. 201880032911.9 dated Nov. 3, 2021 (11 pages) with English Summary.
"Non-Final Office Action," for U.S. Appl. No. 17/101,900 dated Sep. 20, 2021 (48 pages).
"Notice of Allowance," for U.S. Appl. No. 14/883,895 dated Oct. 22, 2021 (18 pages).
"Response to Communication Pursuant to Rules 161(1) and 162 EPC," for European Patent Application No. 19828373.1 filed Nov. 8, 2021 (22 pages).
"Response to Communication Pursuant to Rules 161(1) and 162 EPC," for European Patent Application No. 19836341.8 filed Jan. 7, 2022 (12 pages).
"Response to Communication Pursuant to Rules 70(2) and 70a(2)/ Rule 39(1)," for European Patent Application No. 20214733.6 filed Nov. 23, 2021 (4 pages).
"Response to Non-Final Rejection," dated Sep. 20, 2021 for U.S. Appl. No. 17/101,900, submitted via EFS-Web on Dec. 20, 2021, 10 pages.
"Second Office Action," for Chinese Patent Application No. 201780065376.2 dated Nov. 16, 2021 (8 pages) with English Summary.
"Written Submission," in Response to Summons to Attend Oral Proceedings for European Patent Application No. 18731579.1 filed Nov. 30, 2021 (31 pages).
Groves, William A., et al. "Analysis of Solvent Vapors in Breath and Ambient Air with a Surface Acoustic Wave Sensor Array," Ann. Occup. Hyg., vol. 45, No. 8, pp. 609-623, 2001 (15 pages).
"Decision of Rejection," for Chinese Patent Application No. 201780065376.2 dated Apr. 1, 2022 (9 pages) with English Translation.
"Non-Final Office Action," for U.S. Appl. No. 17/101,900 dated Mar. 31, 2022 (16 pages).
"Response to Communication Pursuant to Article 94(3) EPC," for European Patent Application No. 17733246.7 filed May 18, 2022 (9 pages).

"International Preliminary Report on Patentability," for PCT Application No. PCT/US2019/065981 dated Jul. 1, 2021 (8 pages).
"International Search Report and Written Opinion," for PCT Application No. PCT/US2021/026778 dated Aug. 3, 2021 (11 pages).
"New Summons to Attend Oral Proceedings," for European Patent Application No. 18731579.1 mailed Jul. 12, 2021 (6 pages).
"Notice of Allowance," for U.S. Appl. No. 15/621,103 dated Aug. 3, 2021 (18 pages).
"Notice of Allowance," for U.S. Appl. No. 15/787,985 dated Jul. 15, 2021 (14 pages).
"Response to Final Rejection," dated Apr. 22, 2021 and the Advisory Action dated Jul. 8, 2021 for U.S. Appl. No. 15/621,103, submitted via EFS-Web on Jul. 12, 2021, 13 pages.
"Summons to attend oral proceedings pursuant to Rule 115(1) EPC," for European Patent Application No. 18731579.1 dated Jul. 1, 2021 (6 pages).
Planz, B., et al. "The role of urinary cytology for detection of bladder cancer," EJSO (2005) 21, 304-308 (5 pages).
Ramakumar, Sanjay, et al. "Comparison of Screening Methods in the Detection of Bladder Cancer," The Journal of Urology vol. 161, 388-394, Feb. 1999 (7 pages).
Communication Pursuant to Article 94(3) EPC for European Patent Application No. 18731579.1 dated Nov. 10, 2020 (5 pages).
Final Office Action for U.S. Appl. No. 15/787,985 dated Oct. 21, 2020 (21 pages).
First Office Action for Chinese Patent Application No. 201780030595.7 dated Nov. 2, 2020 (12 pages) with English Summary.
Non-Final Office Action for U.S. Appl. No. 15/621,103 dated Oct. 23, 2020 (27 pages).
Office Action for Japanese Patent Application No. 2019-563876 dated Nov. 4, 2020 (3 pages) No English Translation.
"Communication Pursuant to Article 94(3) EPC," for European Patent Application No. 15790739.5 dated Jun. 3, 2022 (5 pages).
"Determination of Carbonyl Compounds By High performance Liquid Chromatography (HPLC)," EPA Method 8315A 1996 (34 pages).
"First Examination Report," for Australian Patent Application No. 2019224011 dated Apr. 9, 2021 (4 pages).
"International Preliminary Report on Patentability," for PCT Application No. PCT/US2019/018741 dated Sep. 3, 2020 (11 pages).
"International Preliminary Report on Patentability," for PCT Application No. PCT/US2019/028870 dated Nov. 5, 2020 (11 pages).
"International Search Report and Written Opinion," for PCT Application No. PCT/US2019/018741 dated May 6, 2019 (17 pages).
"International Search Report and Written Opinion," for PCT Application No. PCT/US2019/028870 dated Aug. 20, 2019 (17 pages).
"International Search Report and Written Opinion," for PCT Application No. PCT/US2020/046829 dated Nov. 18, 2020 (15 pages).
"International Search Report and Written Opinion," for PCT Application No. PCT/US2022/025004 dated Jul. 25, 2022 (15 pages).
"Non-Final Office Action," for U.S. Appl. No. 16/280,635 dated Feb. 10, 2021 (40 pages).
"Non-Final Office Action," for U.S. Appl. No. 16/393,177 dated May 25, 2021 (37 pages).
"Non-Final Office Action," for U.S. Appl. No. 16/712,255 dated Jun. 23, 2022 (64 pages).
"Notice of Allowance," for U.S. Appl. No. 16/280,635 dated Mar. 31, 2021 (14 pages).
"Office Action," for Japanese Patent Application No. 2018-133996 dated Jul. 12, 2022 (4 pages) with English Translation.
"Response to Communication Pursuant to Article 94(3) EPC," for European Patent Application No. 17794832.0 filed Jul. 7, 2022 (8 pages).
"Response to Communication Pursuant to Rules 161(1) and 162 EPC," for European Patent Application No. 19709268.7 filed Apr. 1, 2021 (12 pages).
"Response to Communication Pursuant to Rules 161(1) and 162 EPC," for European Patent Application No. 19733177.0 filed Jun. 4, 2021 (20 pages).
"Response to Examination Report," for Australian Patent Application No. 2019224011 filed Jul. 23, 2021 (22 pages).

(56) References Cited

OTHER PUBLICATIONS

"Response to Non-Final Rejection," dated Feb. 10, 2021 for U.S. Appl. No. 16/280,635, submitted via EFS-Web on Mar. 17, 2021, 16 pages.
"Response to Non-Final Rejection," dated Mar. 31, 2022 for U.S. Appl. No. 17/101,900, submitted via EFS-Web on Jun. 28, 2022, 11 pages.
"Response to Non-Final Rejection," dated May 20, 2021 for U.S. Appl. No. 14/883,895, submitted via EFS-Web on Aug. 19, 2021, 12 pages.
Agbonlahor, Osazuwa, et al. "Adsorbed Molecules as Interchangeable Dopants and Scatterers with a van der Waals Bonding Memory in Graphene Sensors," ACS Sens. 2020, 5 (7), 2003-2009 (13 pages).
Allen, Matthew J., et al. "Honeycomb Carbon: A Review of Graphene," Chem. Rev. 2010, 110, 132-145 (14 pages).
An, Xiaohong, et al. "Stable Aqueous Dispersions of Noncovalently Functionalized Graphene from Graphite and their Multifunctional High-Performance Applications," Nano Lett. 2010, 10, 4295-4301 (7 pages).
Bair, Kenneth W., et al. "(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).
Bard, Allen J., et al. "Electrochemical Methods: Fundamentals and Applications," Wiley New York: 1980; vol. 2 (850 pages).
Bartosik, Miroslav, et al. "The mechanism and suppression of physisorbed-water caused hysteresis in graphene FET sensors," ACS Sens., vol. 5, 2940-2949 (2020). (40 pages).
Biedermann, Frank, et al. "Experimental Binding Energies in Supramolecular Complexes," Chem. Rev. 2016, 116(9), 5216-5300 (85 pages).
Bock, Harald, et al. "Helicenes from Diarylmaleimides," Organic Letters 2014, 16, 1546-1549 (5 pages).
Boeseken, J. "The Use of Boric Acid for the Determination of the Configuration of Carbohydrates," Adv. Carbohydr. Chem. 1949, 4, 189-210 (22 pages).
Brust, Mathias, et al. "Novel Gold-Dithiol Nano-Networks with Non-Metallic Electronic Properties," Adv. Mater. 1995, 7, No. 9 795-797 (3 pages).
Brust, Mathias, et al. "Synthesis of Thiol-derivatised Gold Nanoparticles in a Two-phase Liquid-Liquid System," J. Chem. Soc., Chem. Commun., 1994, 801-802 (2 pages).
Cancilla, Devon A., et al. "O-(2,3,4,5,6-Pentafluorophenyl)methylhydroxylamine hydrochloride: a versatile reagent for the determination of carbonyl-containing compounds," Journal of Chromatography, 627 (1992) 1-16 (16 pages).
Cao, Mengmei, et al. "Electrochemical and Theoretical Study of $\pi$-$\pi$ stacking Interactions between Graphitic Surfaces and Pyrene Derivatives," J. Phys. Chem. C 2014, 118(5), 2650-2659 (10 pages).
Capuano, Rosamaria, et al. "Corroles-Porphyrins: A Teamwork for Gas Sensor Arrays," Sensors, 2015, vol. 15, pp. 8121-8130 (10 pages).
Chen, Gugang, et al. "Sub-ppt gas detection with pristine graphene," Applied Physics Letters 101, 053119 (2012) 6 pages.
Cheng, Zengguang, et al. "Suspended Graphene Sensors with Improved Signal and Reduced Noise," Nano Lett. 2010, 10, 1864-1868 (5 pages).
Connors, Kenneth A., et al. "The Stability of Cyclodextrin Complexes in Solution," Chem. Rev. 1997, 97, 1325-1357 (34 pages).
Cui, Menghua, et al. "Graphene-organic two-dimensional charge transfer complexes: inter-molecular electronic transitions and broadband near infrared photoresponse," J. Phys. Chem. C 2018, 122 (13), 7551-7556 (7 pages).
Dreyer, Daniel, et al. "The chemistry of graphene oxide," Chem. Soc. Rev. 2010, 39(1), 228-240 (13 pages).
Elemans, Johannes A.A.W., et al. "Molecular Materials by Self-Assembly of Porphyrins, Phthalocyanines, and Perylenes," Adv. Mater. 2006, 18, 1251-1266 (16 pages).
Fan, Xuge, et al. "Humidity and CO2 gas sensing properties of double-layer graphene," Carbon 127 (2018) 576-587 (12 pages).
Fogel, Yulia, et al. "Graphitic Nanoribons with Dibenzo[e,l]pyrene Repeat Units: Synthesis and Self-Assembly," Macromolecules 2009, 42, 6878-6884 (7 pages).
Fuchs, Patricia, et al. "Breath gas aldehydes as biomarkers of lung cancer," Int. J. Cancer 2010, 126 (11), 2663-70 (8 pages).
Gao, Zhaoli, et al. "Scalable Production of Sensor Arrays Based on High-Mobility Hybrid Graphene Field Effect Transistors," ACS Applied Materials & Interfac. 2016, 8(41), 27546-27552 (8 pages).
Gautam, Madhav, et al. "Gas sensing properites of graphene synthesized by chemical vapor deposition," Materials and Science Engineering C31 (2011) 1405-1411 (7 pages).
Gavartin, J.L., et al. "The role of nitrogen-related defects in high-k dialectric oxides: Density-functional studies.," Journal of Applied Physics. vol. 97, Issue 5. (15 pages).
Geim, A.K., et al. "The rise of graphene," Nat. Mater. 2007, 6, 183-191 (9 pages).
Georgakilas, Vasilios, et al. "Functionalization of Graphene: Covalent and Non-Covalent Approaches, Derivatives and Applications," Chem. Rev. 2012, 112(11), 6156-6214 (59 pages).
Ghosh, Sujoy, et al. "Effect of 1-Pyrene Carboxylic-Acid Functionalization of Graphene on Its Capacitive Energy Storage," J. Phys. Chem. C 2012, 116, 20688-20693 (6 pages).
Giancane, Gabriele, et al. "State of Art in Porphyrin Langmuir-Blodgett Films as Chemical Sensors," Advances in Colloid and Interface Science, 2012, vol. 171-172, pp. 17-35 (Year: 2012), 19 pages.
Good, Robert J. "Contact angle, wetting, and adhesion: a critical review," J. Adhesion Sci. Technol. 1992, vol. 6, No. 12, pp. 1269-1302 (34 pages).
Gorodetsky, Alon A., et al. "Electrochemistry Using Self-assembled DNA Monolayers on Highly Oriented Pyrolytic Graphite," Langmuir 2006, 22, 7917-7922 (6 pages).
Guo, Zanru, et al. "Light-Switchable Single-Walled Carbon Nanotubes Based on Host-Guest Chemistry," Adv. Funct. Mater. 2013, 23, 5010-5018 (18 pages).
Hasobe, Taku "Photo- and Electro-Functional Self-Assembled Architectures of Porphyrins," Physics Chemistry Chemical Physics, 2012, 14, pp. 15975-15987 (Year: 2012), 13 pages.
Hayasaka, Takeshi, et al. "The influences of temperature, humidity, and O2 on electrical properties of graphene FETs," Sensors & Actuators: B. Chemical 285 (2019) 116-122 (7 pages).
Hill, Ernie W., et al. "Graphene Sensors," IEEE Sensors Journal, vol. 11, No. 12, Dec. 2011 (10 pages).
Hinnemo, Malkolm, et al. "On Monolayer Formation of Pyrenebutyric Acid on Graphene," Langmuir, 2017, vol. 33, No. 14 pp. 3588-3593 (6 pages).
Hockstein, Neil G., et al. "Diagnosis of Pneumonia with an Electronic Nose: Correlation of Vapor Signature with Chest Computed Tomography Scan Findings," The Laryngoscope 2004, 114 (10), 1701-1705 (5 pages).
Hong Chan, Wing, et al. "Optodes based on a calixarene ester for the determination of aldehydes via in situ generation of the Girard's reagent P derivative," Analyst 1998, 123 (12), 2851-2856 (6 pages).
Hsiao, Min-Chien, et al. "Preparation and properties of a graphene reinforced nanocomposite conducting plate," J. Mater. Chem., 2010, 20, 8496-8505 (10 pages).
Hsieh, Chien-Te, et al. "Field emission from various CuO nanostructures," Applied Physics Letters 2003, vol. 83, No. 6 (3 pages).
Huang, Ke-Jing, et al. "Novel electrochemical sensor based on functionalized graphene for simultaneous determination of adenine and guanine in DNA," Colloids and Surfaces B: Biointerfaces 82 (2011) 543-549 (7 pages).
Hunter, Christopher A., et al. "The Nature of $\pi$-$\pi$ Interactions," J. Am. Chem. Soc. 1990, 112, 5525-5534 (10 pages).
Hwang, Michael, et al. "Ultrasensitive detection of nucleic acids using deformed graphene channel field effect biosensors," Nat. Commun. 2020, 11(1) (11 pages).
Iezhokin, I., et al. "Porphyrin molecules boost the sensitivity of epitaxial graphene for NH3 detection," J. Phy.: Condens. Matter 29 (2017) (11 pages).

(56) References Cited

OTHER PUBLICATIONS

Ionescu, Radu, et al. "Detection of Multiple Sclerosis from exhaled Breath Using Bilayers of Polycyclic Aromatic Hydrocarbons and Single-Wall Carbon Nanotubes," ACS Chemical Neurosci. 2011, 2(12), 687-693 (7 pages).
Jiao, Dezhi, et al. "Supramolecular Peptide Amphiphile Vesicles through Host-Guest Complexation," Angew. Chem. Int. Ed. 2012, 51, 9633-9637 (5 pages).
Szejtli, Jozef "Introduction and General Overview of Cyclodextrin Chemistry," Chem. Rev. 1998, 98, 1743-1753 (12 pages).
Kang, Junmo, et al. "Graphene Transfer: key for applications," Nanoscale, 2012, 4, 5527 (11 pages).
Kang, Xinhuang, et al. "Glucose Oxidase-graphene-chitosan modified electrode for direct electrochemistry and glucose sensing," Biosensors and Bioelectronics 25 (2009) 901-905 (5 pages).
Knipp, Ralph J., et al. "A versatile probe for chemoselective capture and analysis of carbonyl compounds in exhaled breath," Anal Methods, 2015, 7, 6027 (7 pages).
Kobayashi, Keiko, et al. "Gas chromatrographic determination of low-molecular-weight carbonyl compounds in aqueous solution as their O-(2,3,4,5,6-pentafluorobenzyl) oximes," Journal of Chromatography A 1980, 187(2), 413-417 (5 pages).
Kozbial, Andrew, et al. "Study on the surface energy of graphene by contact angle measurement," Langmuir 2014, 30 (28), 8598-8606 (28 pages).
Kuila, Tapas, et al. "Chemical functionalization of graphene and its applications," Progress in Materials Science 57 (2012) 1061-1105 (45 pages).
Lauffer, Peter, et al. "Molecular and electronic structure of PTCDA on bilayer graphene on SiC(0001) studied with scanning tunnerling microscopy," Phys. Stat. Sol. (b) 2008, 245, No. 10, 2064-2067 (4 pages).
Lechner, Christoph, et al. "Adhesive Forces Between Aromatic Molecules and Graphene," The Journal of Physical Chemistry C 2014, 118(36), 20970-20981 (12 pages).
Lecourt, Thomas, et al. "Triisobutylaluminium and Diisobutylaluminium Hydride as Molecular Scalpels: The Regioselective Stripping of Perbenzylate Sugars and Cyclodextrins," Chem. Eur. J. 2004, 10, 2960-2971 (12 pages).
Li, Errui, et al. "Aliphatic Aldehyde Detection and Adsorption by Nonporous Adaptive Pillar[4]arene[1]quinone Crystals with Vapochromic Behavior," ACS Applied Materials & Interfaces, 2018, 10, 23147-23153 (23 pages).
Li, Mingxiao, et al. "Preconcentration and Analysis of Trace Volatile Carbonyl Compounds," Anal Chem 2012, 84(3), 1288-1293 (6 pages).
Lienerth, Peter, et al. "Improving the Selectivity to Polar Vapors of OFET-Based Sensors by Using the Tranfser Charactersitics Hysteresis Response," Sensors and Actuators B 225 (2016) 90-95 (6 pages).
Liu, Sophie F., et al. "Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).
Liu, Yifei M., et al. "Electrochemical Sensing of Nitric Oxide with Functionalized Graphene Electrodes," ACS Applied Materials & Interfaces 2013, 5(23), 12624-12630 (7 pages).
Liu, Yuxin, et al. "Biological and Chemical Sensors based on Graphene Materials," Chem. Soc. Rev. 2012, 41 (6), 2283-2307 (27 pages).
Loh, Kian Ping, et al. "The Chemistry of Graphene," J. Mater. Chem., 2010, 20, 2277-2289 (13 pages).
Long, Brenda, et al. "Non-Covalent Functionalization of Graphene Using Self-Assembly of Alkane-Amines," Adv. Funct. Mater. 2012, 22, 717-725 (9 pages).
Lu, Chun-Hua, et al. "A Graphene Platform for Sensing Biomolecules," Angew. Chem. Int. Ed. 2009, 48, 4785-4787 (3 pages).
Mackin, Charles, et al. "Chemiresistive Graphene Sensors for Ammonia Detection," ACS Appl. Mater. Interfaces 2018, 10, 16169-16176 (8 pages).
Mann, Jason A., et al. "Improving the Binding Characteristics of Tripodal Compounds on Single Layer Graphene," American Chemical Society 2013, vol. 7, No. 8, 7193-7199 (7 pages).
Manochehry, Sepehr, et al. "Optical biosensors utilizing graphene and functional DNA molecules," J. Mater. Res. 2017, 32(15), 2973-2983 (11 pages).
Manolis, Antony "The Diagnostic Potential of Breath Analysis," Clin. Chem. 29/1, 5-15 (1983) (11 pages).
Mao, Shun, et al. "Specific Protein Detection Using Thermally Reduced Graphene Oxide Sheet Decorated with Gold Nanoparticle-Antibody Conjugates," Adv. Mater. 2010, 22, 3521-3526 (6 pages).
McCulloch, Michael, et al. "Diagnostic Accuracy of Canine Scent Detection in Early- and Late-Stage Lung and Breast Cancers," Integrative Cancer Therapies 2006, 5(1), 30-39 (11 pages).
Moldoveanu, Serban C., et al. "Derivatization Methods in GC and GC/MS," in Gas Chromatography-Derivatization, Sample Preparation, Application, Kusch, P., Ed. IntechOpen:2018 (33 pages).
Muruganathan, Manoharan, et al. "Electrically Tunable van der Waals Interaction in Graphene—Molecule Complex," Nano Lett. 2015, 15(12), 8176-8180 (5 pages).
Nag, Sanada, et al. "Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).
Novoselov, K.S., et al. "Electric Field Effect in Atomically Thin Carbon Films," Science 2004, 306, 666-669 (5 pages).
Ohno, Yasuhide, et al. "Electrolyte-Gated Graphene Field-Effect Transistors for Detecting pH and Protein Adsorption," Nano Letters 2009, vol. 9, No. 9, 3318-3322 (5 pages).
Olson, Eric J., et al. "Getting More out of a Job Plot: Determination of Reactant to Product Stoichiometry in Cases of Displacement Reactions and n:n Complex Formation," J. Org. Chem. 2011, 76, 8406-8412 (7 pages).
Ou, Baoli, et al. "Covalent functionalization of graphene with poly(methyl methacrylate) by atom transfer radical polymerization at room temperature," Polym. Chem., 2012, 3, 2768 (8 pages).
Park, Eun Uk, et al. "Correlation between the sensitivity and the hysteresis of humidity sensors based on graphene oxides," Sensors and Actuators B 258 (2018) 255-262 (8 pages).
Pathipati, Srinivasa Rao, et al. "Modulation of charge transport properties of reduced graphene oxide by submonolayer physisorption of an organic dye," Organic Electronics 14 (2013) 1787-1792 (6 pages).
Peng, Gang, et al. "Diagnosing lung cancer in exhaled breath using gold nanoparticles," Nature nanotechnology, 2009, 4(10), 669-673 (5 pages).
Peressi, Maria "Surface Functionalization of Graphene," Graphene Chemistry, John Wiley & Sons, Ltd:2013, pp. 233-253 (21 pages).
Poli, Diana, et al. "Determination of aldehydes in exhaled breath of patients with lung cancer by means of on-fiber-derivatisation SPME-GC/MS," Journal of Chromatography B, 878 (2010) 2643-2651 (9 pages).
Poulston, S., et al. "Surface Oxidation and Reduction of CuO and Cu2O Studied Using XPS and XAES," Surface and Interface Analysis, vol. 24, 811-820, 1996, (10 pages).
Pyo, Soonjae, et al. "Improved photo- and chemical-responses of graphene via porphyrin-functionalization for flexible, transparent, and sensitive sensors," Nanotechnology 30 (2019) 215501 (9 pages).
Rekharsky, Mikhail V., et al. "Complexation Thermodynamics of Cyclodextrins," Chem. Rev. 1998, 98, 1875-1917 (44 pages).
Reuillard, B., et al. "Non-covalent double functionalization of carbon nanotubes wiht a NADH oxidation Ru(II)-based molecular catalyst and a NAD-dependent glucose dehydrogenase," Chem. Commun. 2014, 50(79), 11731-11734 (5 pages).
Rodner, Marius, et al. "Graphene Decorated with Iron Oxide Nanoparticles for Highly Sensitive Interaction with Volatile Organic Compounds," Sensors 2019, 19, 918-026 (9 pages).
Rushi, A.D., et al. "Exercising Substituents in porphyrins for real time selective sensing of volatile organic compounds," Sensors and Actuators B: Chemical, vol. 257, 2018, pp. 389-397 (9 pages).
Schedin, F., et al. "Detection of Individual Gas Molecules Adsorbed on Graphene," Nat. Mater. 2007, 6(9), 652-655 (11 pages).

(56) References Cited

OTHER PUBLICATIONS

Shao, Yuyan "Graphene Based Electrochemical Sensor and Biosensors: A Review," Electroanalysis 2010, 22, No. 10, 1027-1036 (10 pages).
Shao, Yuyan, et al. "Nitrogen-doped graphene and its electrochemical applications," J. Mater. Chem., 2010, 20, 7491-7496 (6 pages).
Song, Nan, et al. "Applications of pillarenes, an emerging class of synthetic macrocycles," Science China Chemistry, 2014, 57(9), 1185-1198 (15 pages).
Su, Qun, et al. "Understanding Sources of Electrical Disorder in Graphene Grown by Chemical Vapor Deposition for Wafer-Scale Device Applications," ACS Appl. Nano Mater., vol. 2 (2019) 3426-3433 (26 pages).
Suk, Ji Won, et al. "Transfer of CVD-Grown Monolayer Graphene onto Arbitrary Substrates," ACS Nano 2011, 5(9), 6916-6924 (10 pages).
Swanson, Emily, et al. "Self Assembly of Monolayers on Graphene with Pyrene and Cyclodextrin Derivatives," Research Poster. Elon University, LANDO program, Research Experience for Undergraduates Program of the National Science Foundation, Council of Undergraduate Research Experiences for Undergraduates symposium in Washington, D.C., Oct. 23-24, 2016 (1 page).
Terse-Thakoor, Trupti, et al. "Graphene based biosensors for healthcare," J. Mater. Res. 2017, 32(15), 2905-2929 (25 pages).
Turkevich, John, et al."A study of the nucleation and growth processes in the synthesis of colloidal gold," Discuss. Faraday Soc., 1951,11, 55-75 (23 pages).
Vincent, Mark A., et al."Accurate Prediction of Adsorption Energies on Graphene, Using a Dispersion-Corrected Semiempirical Method Including Solvation," J. Chem. Inf. Model. 2014, 54, 2225-2260 (6 pages).
Wang, Lihua "A novel [beta]-cyclodextrin Functionalized Reduced Graphene Oxide Electrochemical Sensor for Blood Glucose Detection," International Journal of Electrochemical Science, Published Dec. 28, 2017 pp. 1594-1602 (9 pages).
Wang, Qing Hua, et al. "Room-temperature molecular-resolution characterization of self-assembled organic monolayers on epitaxial graphene," Nature Chemistry 2009 vol. 1 (3), 206-211 (6 pages).
Wei, Jinwei, et al. "Understanding asymmetric transfer characteristics and hysteresis behaviors in graphene devices under different chemical atmospheres," Carbon 156 (2020) 67-76 (10 pages).
Wu, Ting, et al. "Quantitative principles for precise engineering of sensitivity in carbon-based electrochemical sensors," Adv. Mater. 2018,1805752 (27 pages).
Xu, Yuxi, et al. "Flexible Graphene Films via te Filtration of Water-Soluble Noncovalent Functionalized Graphene Sheets," J. Am. Chem. Soc. 2008, 130, 5856-5857 (2 pages).
Xu, Huifeng, et al. "Direct Electrochemixtry and electrocatalysis of hemoglobin protein entrapped in graphene and chitosan composite film," Talanta 81 (2010) 334-338 (5 pages).
Xu, Mengjian, et al. "Gate-polarity-dependent doping effects of H2O adsorption on graphene/SiO2 field-effect transistors," J. Phys. D: Appl. Phys. 53 455301, 2020, (8 pages).
Xu, Shicai, et al. "Real-time reliable determination of binding kinetics of DNA hybridization using a multi-channel graphene biosensor," Nat. Commun. 2017, 8(1) 11 pages.
Yavari, Fazel, et al. "Graphene-Based Chemical Sensors," J. Phys. Chem. Lett. 2012, 3, 1746-1753 (8 pages).
Yildiz, Ibrahim "A DFT Approach to the Mechanistic Study of Hydrozone Hydrolysis," J. Phys. Chem. A 2016, 120 (20), 3683-92 (25 pages).
Zhang, Yiheng, et al. "Direct Measurements of the Interaction between Pyrene and Graphite in Aqueous Media by Single Molecule Force Spectroscopy: Understanding the π-π Interactions," Langmuir 2007, 23, 7911-7915 (5 pages).
Zhao, Yan-Li, et al. "Noncovalent Functionalization of Single-Walled Carbon Nanotubes," Accounts of Chemical Research 2009, vol. 42, No. 8. 1161-1171 (12 pages).
Zheng, Peiru, et al. "Oxidation of graphene with variable defects: alternately symmetrical escape and self-restructuring of carbon rings," Nanoscale 2020, 12 (18), 10140-10148 (10 pages).
Zhu, Congzhi, et al. "Mingling Electronic Chemical Sensors with Supramolecular Host-Guest Chemistry," Current Organic Chemistry, 2014, 18, 1957-1964 (8 pages).
Zhu, Yanwu, et al. "Graphene and Graphene Oxide: Synthesis, Properties, and Applications," Adv. Mater. 2010, 22, 3906-3924 (19 pages).
"Communication Pursuant to Article 94(3) EPC," for European Patent Application No. 20214733.6 dated Jan. 16, 2023 (5 pages).
"International Preliminary Report on Patentability," for PCT Application No. PCT/US2021/026778 dated Nov. 10, 2022 (7 pages).
"Non-Final Office Action," for U.S. Appl. No. 17/101,900 dated Nov. 4, 2022 (19 pages).
"Notice of Allowance," for U.S. Appl. No. 16/712,255 dated Jan. 20, 2023 (31 pages).
"Notice of Allowance," for U.S. Appl. No. 17/101,900 dated Feb. 28, 2023 (31 pages).
"Response to Communication Pursuant to Article 94(3) EPC," for European Patent Application No. 15790739.5 filed Oct. 12, 2022 (35 pages).
"Response to Non-Final Rejection," dated Jun. 23, 2022 for U.S. Appl. No. 16/712,255, submitted via EFS-Web on Sep. 22, 2022, 7 pages.
"Communication Pursuant to Article 94(3) EPC," for European Patent Application No. 17794832.0 dated Mar. 16, 2023 (7 pages).
"Response to Communication Pursuant to Article 94(3) EPC," for European Patent Application No. 20214733.6 filed May 23, 2023 (45 pages).
"Second Office Action," for Chinese Patent Application No. 201810782878.3 dated Feb. 25, 2023 (4 pages) with English Summary.
"First Office Action," for Chinese Patent Application No. 201980077885.6 dated Aug. 30, 2023 (10 pages) with English Summary.

* cited by examiner

SYSTEMS AND METHODS FOR DETECTING A HEALTH CONDITION

This application claims the benefit of U.S. Provisional Application No. 62/771,856, filed Nov. 27, 2018, the content of which is herein incorporated by reference in its entirety.

FIELD

Embodiments herein relate to systems and methods for detecting a health condition in a subject. More specifically, the embodiments herein related to systems and methods for detecting a health condition by analyzing volatile organic compounds emitted from a biological sample of a subject.

BACKGROUND

Disease states can cause inflammation in a subject due to oxidative stress that can change the affected cells' metabolism and result in the production of volatile organic compounds that are unique to a disease state. However, a biopsy of a suspect tissue, liquid, or solid sample can be limited in size and quality and can thus limit the amount of metabolic byproducts available for making an accurate detection of a disease state.

Current detection methods have various drawbacks, including requiring large sample sizes, sedation of a subject at a medical facility for on-site detection, or costly equipment. Some detection methods may not provide useful information until after significant damage to and/or impairment of the individual has already taken place.

SUMMARY

In a first aspect, a method for detecting a health condition of a subject is included. The method includes obtaining a biological sample from the subject and placing it into a container having a headspace surrounding the biological sample. The method can include contacting a gas from the headspace with a chemical sensor element, the chemical sensor element including one or more discrete graphene varactors. The method can include sensing and storing capacitance of the discrete graphene varactors to obtain a sample data set.

In a second aspect, in addition to one or more of the preceding or following aspects, or in the alternative to some aspects, the method can include classifying the sample data set into one or more preestablished classifications.

In a third aspect, in addition to one or more of the preceding or following aspects, or in the alternative to some aspects, the method can include identifying a therapy to treat the subject based on the preestablished classification.

In a fourth aspect, in addition to one or more of the preceding or following aspects, or in the alternative to some aspects, the method can include identifying a drug therapy to treat the subject based on the preestablished classification.

In a fifth aspect, in addition to one or more of the preceding or following aspects, or in the alternative to some aspects, the method can include identifying a device therapy to treat the subject based on the preestablished classification.

In a sixth aspect, in addition to one or more of the preceding or following aspects, or in the alternative to some aspects, the headspace above or around the biological sample includes a volume of a gas.

In a seventh aspect, in addition to one or more of the preceding or following aspects, or in the alternative to some aspects, the container is flushed with an inert gas prior to placing the biological sample into the container.

In an eighth aspect, in addition to one or more of the preceding or following aspects, or in the alternative to some aspects, the container includes a sample port, where the biological sample is placed into the container through the sample port.

In a ninth aspect, in addition to one or more of the preceding or following aspects, or in the alternative to some aspects, the gas from the headspace is continuously drawn from the container and contacted with the chemical sensor element.

In a tenth aspect, in addition to one or more of the preceding or following aspects, or in the alternative to some aspects, the biological sample is incubated in the container.

In an eleventh aspect, in addition to one or more of the preceding or following aspects, or in the alternative to some aspects, the biological sample is incubated in the container for a period of time before the gas from the headspace is contacted with a chemical sensor element.

In a twelfth aspect, in addition to one or more of the preceding or following aspects, or in the alternative to some aspects, the biological sample is incubated at physiological temperature.

In a thirteenth aspect, in addition to one or more of the preceding or following aspects, or in the alternative to some aspects, the biological sample is incubated in a culture medium.

In a fourteenth aspect, in addition to one or more of the preceding or following aspects, or in the alternative to some aspects, the biological sample is heated to a temperature in the range of 25 degrees C. to 40 degrees C. prior to contacting the headspace with a chemical sensor element.

In a fifteenth aspect, in addition to one or more of the preceding or following aspects, or in the alternative to some aspects, the health condition includes a disease state including a cancer.

In a sixteenth aspect, in addition to one or more of the preceding or following aspects, or in the alternative to some aspects, where obtaining a biological sample includes obtaining one or more of an organ biopsy, blood, urine, bile, sweat, feces, lymph, cerebrospinal fluid, amniotic fluid, pericardial fluid, peritoneal fluid, saliva, synovial fluid, serous fluid, sebum, bone biopsy, muscle biopsy, cheek swab biopsy, or isolated cells.

In a seventeenth aspect, in addition to one or more of the preceding or following aspects, or in the alternative to some aspects, the sample data set is used to detect the presence of pathogenic bacteria within the biological sample.

In an eighteenth aspect, in addition to one or more of the preceding or following aspects, or in the alternative to some aspects, volatile organic compounds (VOCs) from the biological sample that are present in the gas from the headspace interface with the discrete graphene varactors to influence sensed capacitance.

In a nineteenth aspect, in addition to one or more of the preceding or following aspects, or in the alternative to some aspects, the sample data set is analyzed to determine an improvement or a worsening in a disease state of the subject over a period of time greater than 24 hours.

In a twentieth aspect, in addition to one or more of the preceding or following aspects, or in the alternative to some aspects, where sensing and storing capacitance of the graphene varactors to obtain a sample data set is performed across a range of bias voltages.

In a twenty-first aspect, in addition to one or more of the preceding or following aspects, or in the alternative to some aspects, the range of bias voltages is from −3 V to 3 V.

In a twenty-second aspect, in addition to one or more of the preceding or following aspects, or in the alternative to some aspects, where at least 40 discrete capacitance values are stored for each graphene varactor across the range of bias voltages.

In a twenty-third aspect, in addition to one or more of the preceding or following aspects, or in the alternative to some aspects, the method can include storing additional data regarding the subject beyond sensed capacitance as part of the sample data set that is classified.

In a twenty-fourth aspect, in addition to one or more of the preceding or following aspects, or in the alternative to some aspects, the additional data can include at least one of: prior disease states of the subject; age of the subject; results of a physical examination; symptoms experienced by the subject; and data regarding specific biomarkers of one or more disease states.

In a twenty-fifth aspect, a container for detecting a disease state is included. The container can include a housing adapted to contain a biological sample of a subject, the housing defining a headspace including a volume of a gas. The container can include a chemical sensor element in fluid communication with the headspace, the chemical sensor element including one or more discrete graphene varactors.

In a twenty-sixth aspect, in addition to one or more of the preceding or following aspects, or in the alternative to some aspects, the container can include a gas inlet conduit and a gas outlet conduit, the gas outlet conduit configured to be in fluid communication with the chemical sensor element.

In a twenty-seventh aspect, in addition to one or more of the preceding or following aspects, or in the alternative to some aspects, the container can include a chemical sensor chamber, where the chemical sensor element is disposed in the chemical sensor chamber. The container can include a movable sealing member that can move between a first position and a second position. The chemical sensor element disposed in the chemical sensor chamber is in selective fluid communication with the headspace, where movement between the first position and the second position exposes the chemical sensor chamber to fluid communication with the headspace.

In a twenty-eighth aspect, in addition to one or more of the preceding or following aspects, or in the alternative to some aspects, the movable sealing member is a plunger.

In a twenty-ninth aspect, in addition to one or more of the preceding or following aspects, or in the alternative to some aspects, the volume of the gas in the headspace includes 0.5% to 50% of a total volume of the container.

In a thirtieth aspect, in addition to one or more of the preceding or following aspects, or in the alternative to some aspects, the gas including an inert gas.

In a thirty-first aspect, in addition to one or more of the preceding or following aspects, or in the alternative to some aspects, the container can include a sample port for placing a biological sample into the container.

In a thirty-second aspect, in addition to one or more of the preceding or following aspects, or in the alternative to some aspects, the container can include a partition that is configured to be opened or closed during use.

In a thirty-third aspect, a method of treating a subject for a disease state is included. The method can include obtaining a biological sample from the subject and placing it into a container having a headspace above or around the biological sample. The method can include contacting a gas from the headspace with a chemical sensor element, the chemical sensor element including one or more discrete graphene varactors. The method can include sensing and storing capacitance of the discrete graphene varactors to obtain a sample data set. The method can include classifying the sample data set into one or more preestablished disease state classifications. The method can include identifying a therapy to treat the subject based on the disease state classification.

In a thirty-fourth aspect, in addition to one or more of the preceding or following aspects, or in the alternative to some aspects, the method can include treating the subject based on the disease state classification including a drug therapy.

In a thirty-fifth aspect, in addition to one or more of the preceding or following aspects, or in the alternative to some aspects, the method can include treating the subject based on the disease state classification including a device therapy.

In a thirty-sixth aspect, a system for detecting a disease state in a subject is included. The system can include a container. The container can include a housing adapted to contain a biological sample of a subject, the housing defining a headspace. The system can include a chemical sensor element, the chemical sensor element including one or more discrete graphene varactors.

In a thirty-seventh aspect, in addition to one or more of the preceding or following aspects, or in the alternative to some aspects, the system can include a heat source.

In a thirty-eighth aspect, in addition to one or more of the preceding or following aspects, or in the alternative to some aspects, the container can include a gas inlet port and a gas outlet port, the gas outlet port configured to be in fluid communication with the chemical sensor element.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

A health condition, such as disease state within a subject, can result in a change in metabolism for affected cells, which can in turn result in the production of volatile organic compounds (VOCs) by the affected cells. Detection of VOCs within tissues, liquids, or solids of a subject can be of substantial diagnostic value to help provide appropriate care and/or treatment to a subject after onset of a diseased state or other medical event. In some cases, VOCs and/or patterns of emission regarding the same can be detected in small concentrations from a biological sample of a subject.

A biological sample can be placed in a container and gasses emitted into the headspace environment therein can be measured for VOC content. A graphene sensor array can be exposed to the gasses from the headspace of the vessel and analyzed for a pattern of response specific to a particular health condition, such as a disease state. Typically, VOCs associated with a healthy biological sample of a subject will have a different pattern of response from the graphene sensor as compared to VOCs associated from an affected biological sample.

In accordance with embodiments herein, various VOCs can be detected within a biological sample of a subject to aid in the diagnosis of a disease state and/or as a part of methods of treating or caring for the same. In various embodiments, one or more VOCs can be detected in a biological sample of a subject where the biological sample is of limited size. In other embodiments, analysis of VOCs can be performed rapidly in the field, beyond just in a care facility.

In some embodiments, detection of VOCs and/or patterns related to the same for a period of time following onset a disease can be used to monitor progress in response to a treatment or to alter a course of treatment as needed.

Figure 1:
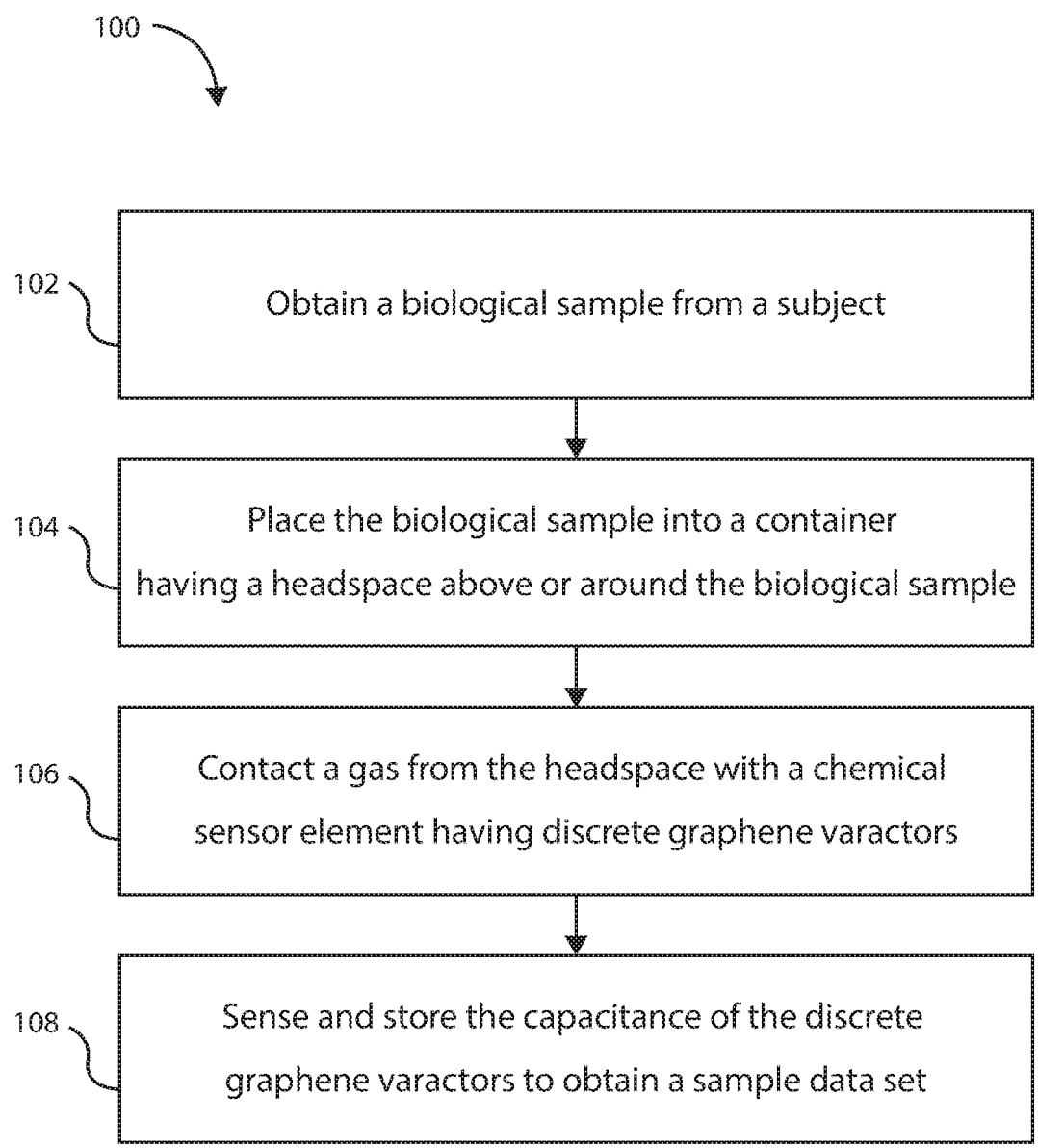
FIG. 1 is a schematic flow diagram of a method for detecting a health condition in accordance with various embodiments herein.

Referring now to FIG. 1, a schematic view of a method 100 for detecting a health condition, such as a disease state, in a subject is shown in accordance with various embodiments herein. The method 100 for detecting a disease state can include obtaining a biological sample from the subject at 102. The method 100 can include placing the biological sample into a container having a headspace above or around the biological sample at 104. The method 100 can include contacting a gas from the headspace with a chemical sensor element at 106. The chemical sensor element can include a plurality of discrete graphene varactors, which will be discussed below in reference to FIGS. 12, 14-17. The method 100 can include sensing and storing the capacitance of the discrete graphene varactors to obtain a sample data set at 108. In some embodiments the subject is a human. In other embodiments, the subject is an animal, including, but not to be limited to, a cow, bison, pig, sheep, goat, horse, dog, cat, and chicken. In some embodiments, the biological sample can be from another type of life form, such as a microbe or a plant.

Obtaining a biological sample from a subject can include, obtaining a biological sample during a routine physical examination, obtaining a biological sample following onset of a disease or other medical event, obtaining a biological sample at various time periods following the onset of a disease state or other medical event, and the like. Biological samples can be obtained from a subject as part of a biopsy procedure, a phlebotomy procedure, a buccal swab procedure, a urine collection process, and the like. Other methods for obtaining a biological sample and types of biological samples will be discussed elsewhere herein.

In some embodiments, obtaining a biological sample from a subject can include obtaining a biological sample immediately following the onset of a disease state or other medical event. In some embodiments, obtaining a biological sample from a subject can include obtaining a biological sample one day following the onset of a disease state or other medical event, one week following the onset of a disease state or other medical event, two weeks following the onset of a disease state or other medical event, one month following the onset of a disease state or other medical event, six months following the onset of a disease state or other medical event, or one year following the onset of a disease state or other medical event. In other embodiments, obtaining a biological sample from a subject can include obtaining a biological sample more than one year following the onset of a disease state or other medical event. In some embodiments, obtaining a biological sample from a subject can include obtaining a biological sample at any of the forgoing times to monitor progression of a treatment for a disease state.

The gas within a headspace above or around a biological sample of a subject can be sampled multiple times over a course of monitoring a subject for a health condition, such as a disease state. The gas can be sampled at various time points following the collection of a sample and/or the onset of a disease state or other medical event. The time points for sampling a gas can include, but not be limited to immediately after the onset of a disease state or other medical event or obtaining a biological sample, within 60 minutes following the onset of a disease state or other medical event or obtaining a biological sample, and within 1 day following the onset of a disease state or other medical event or obtaining a biological sample. The gas within a headspace above or around a biological sample of a subject can be sampled at additional time points following the onset of a disease state or other medical event or obtaining a biological sample, including at 5 minutes, 10 minutes, 20 minutes, 30 minutes, 40 minutes, 50 minutes, 1 hour, 1.5 hours, 2 hours, 2.5 hours, 3 hours, 4 hours, 4.5 hours, 5 hours, 6 hours, 7 hours, 8 hours, 9 hours, 10 hours, 11 hours, 12 hours, 18 hours, 24 hours, 48 hours, or at various time points between any of the foregoing. In some embodiments, a gas within a headspace above or around a biological sample can be sampled at greater than 48 hours. In other embodiments, a gas within a headspace above or around a biological sample can be sampled only once at the time of collection.

Figure 2:
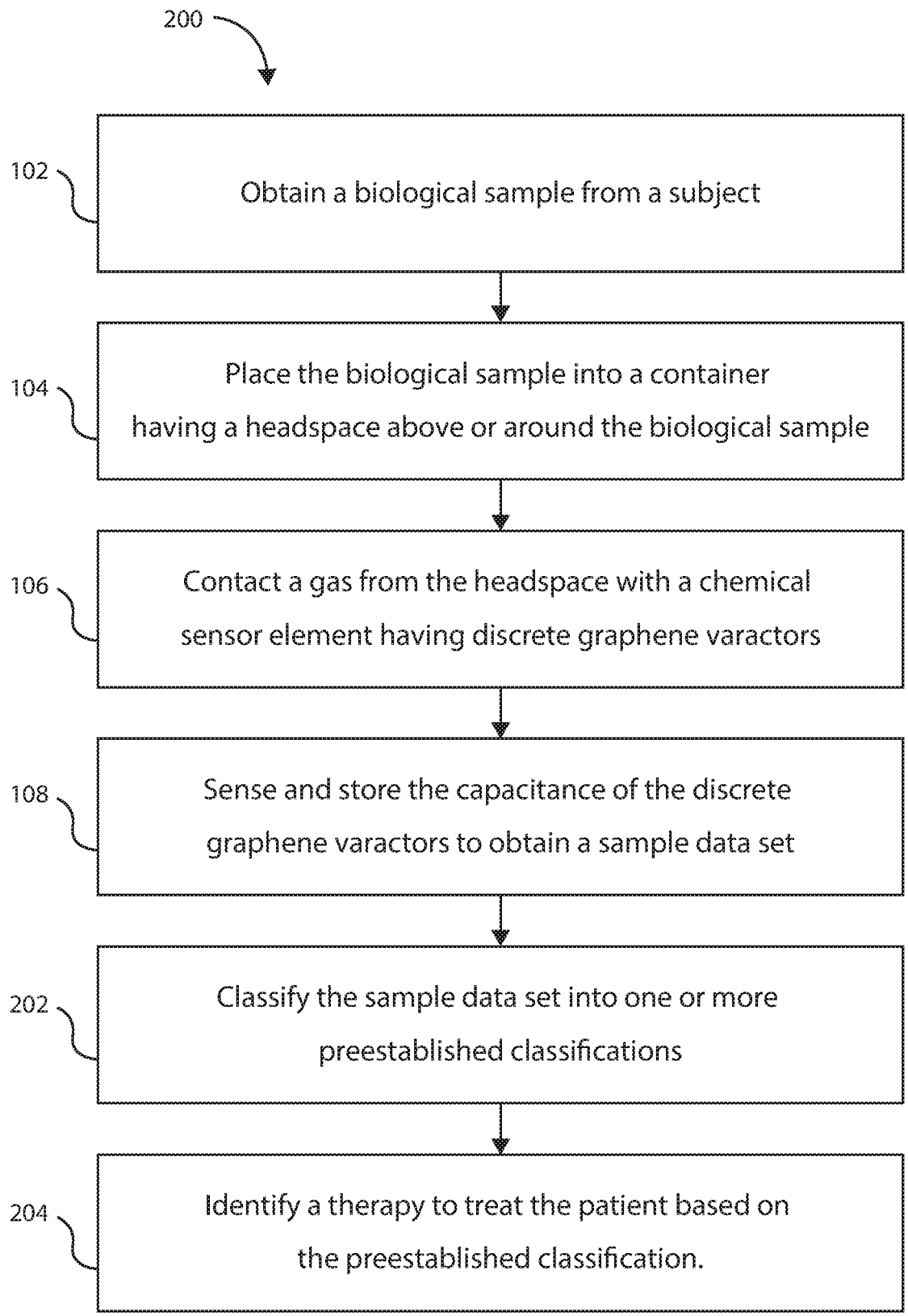
FIG. 2 is a schematic flow diagram of an additional method for detecting a health condition in accordance with various embodiments herein.

Referring now to FIG. 2, a schematic view of a method 200 for detecting a disease state in a subject is shown in accordance with various embodiments herein. Method 200 can include steps 102, 104, 106, and 108 as discussed above with respect to FIG. 1. Method 200 can also include classifying the sample data set into one or more preestablished classifications at 202. The one or more preestablished classifications will be discussed in more detail below. The method 200 can also include identifying a therapy 204 to treat the subject based on the preestablished classifications. In some embodiments the therapy can also include treating the subject with a drug therapy, while in other embodiments the therapy can include treating the subject with a device therapy.

In some embodiments, analyzing the sample data set can include determining an improvement or a worsening of a disease state of a subject over a period of time, such as 30 minutes. In some embodiments, analyzing the sample data set can include determining an improvement or a worsening of a disease state of a subject over 24 hours to 48 hours. In some embodiments, analyzing the sample data set can include determining an improvement or a worsening of a disease state of a subject over 24 hours to 72 hours. In other embodiments, the method can include analyzing the sample data set to determine an improvement or a worsening of a disease state of a subject over 1 week to 2 weeks or more. The sample data set can be further analyzed to identify if the subject is a candidate for rehabilitation treatment, device therapy, interventional therapy, or drug therapy for the disease state.

Sensing and storing capacitance of the graphene varactors to obtain a sample data set can be performed across a range of bias voltages. In some embodiments, the sensing and storing of capacitance of the graphene varactors can include sensing the capacitance from −3 V to 3 V. In some embodiments, the range of bias voltages can be from −2 V to 2 V. In other embodiments, the range of voltages can be from −1.5 V to 1.5 V. In some embodiments, the sensing of capacitance of the graphene varactors can include sensing the capacitance at −3 V, −2.5 V, −2.0 V, −1.5 V, −1.0 V, −0.5 V, 0.5 V, 1.0 V, 1.5 V, 2.0 V, 2.5 V, 3.0 V. It will be appreciated that the sensing and storing of capacitance of the graphene varactors can include sensing the capacitance within a range, wherein any of the forgoing voltages can serve as the lower or upper bound of the range, provided that the lower bound of the range is a value less than the upper bound of the range.

The sensing and storing of capacitance of the graphene varactors across a range of bias voltages can include sensing the capacitance in a stepped fashion. Sensing and storing of capacitance in a stepped fashion can be performed at voltage intervals, such as every 5 mV, 10 mV, 25 mV, 50 mV, 75 mV, 100 mV, 125 mV, 150 mV, 200 mV, 300 mV, 400 mV, or 500 mV, or by a stepped amount falling within a range between any of the foregoing.

When sensing and storing of capacitance of the graphene varactors across a range of bias voltages in a stepped fashion, a sample data set can be obtained at each bias voltage for each discrete graphene varactor. The sensing and storing of capacitance of the graphene varactors across a range of bias voltages to obtain a sample data set can include storing at least 10, 20, 30, 40, 50, 60, 70, 80, 90, 100, 125, 150, 175, 200, 250, 300, 350, 400, 450, 500, or more discrete capacitance values (or a number of discrete capacitance values falling within a range between any of the foregoing) for each graphene varactor across the range of bias voltages.

The methods herein can also include gathering and/or storing additional data regarding the subject beyond sensed capacitance as part of the sample data set that is classified. The additional data can include, but not be limited to prior disease states of the subject; the time elapsed since a past disease state of the subject; age of the subject; results of one or more physical examinations; symptoms experienced by the subject; and data regarding specific biomarkers of one or more disease states. The additional data can also include information regarding past treatment regimens, and successes or failures of past treatment regimens.

It will be appreciated that VOCs present in a gas from a headspace over a biological sample can interface with the discrete graphene varactors of the chemical sensor to influence sensed capacitance. The VOCs emitted by a biological sample of a subject in a disease state can be different (in terms of type, amount, etc.) than the VOCs in a biological sample of a subject in a non-disease state. One or more biological samples can be obtained from a subject during routine physical examination prior to the onset of a disease state or other medical event. The data obtained from sensing and storing capacitance from the biological sample in a non-disease state can serve as a baseline value. Examples of obtaining a biological sample in a non-disease state can include, but are not limited to, obtaining a biological sample during a routine physical examination, obtaining a biological sample prior to deployment for military duty, obtaining a biological sample prior to undertaking an exercise or athletic regimen, etc., on a daily, weekly, or monthly basis. In some embodiments, data from a biological sample can be obtained from a subject in a clinical setting as part of a routine physical examination and can serve as a baseline for the VOC content in that subject's biological sample should disease occur at some point in the future.

Figure 3:
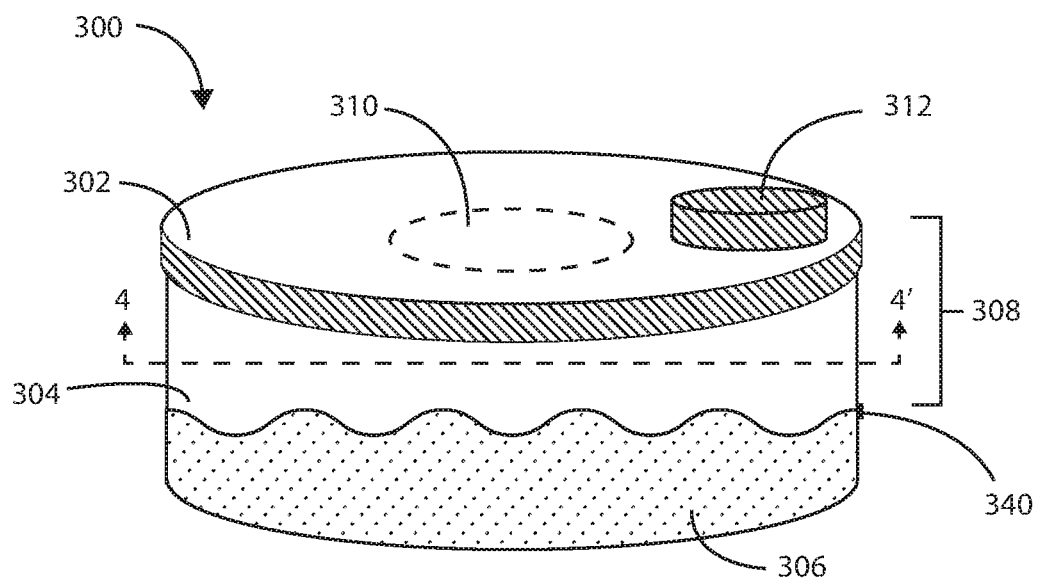
FIG. 3 is a schematic diagram of a container in accordance with various embodiments herein.

Exemplary containers suitable for use with the methods herein will be described in reference to FIGS. 3-12. Referring now to FIG. 3, a schematic diagram of a container 300 for detecting a disease state is shown in accordance with various embodiments herein. Container 300 can include a lid 302, and base housing 304. The base housing 304 can be adapted to contain a biological sample 306 of a subject. The lid 302 can be removably attached to the base housing 304 so as to form a headspace 308 within the container 300. As used herein, "headspace" can refer to a volume of gas above or surrounding a biological sample.

It will be appreciated that in some embodiments, the lid 302 can be integral with the base housing 304 to seal off the internal environment of the container 300 from the external environment. In such embodiments, container 300 can include a sample port 312 for placing a biological sample into the container 300. The sample port 312 can be removably connected to the container 300 or it can be integral with the container 300. In some embodiments, sample port 312 can include a polymeric material that can be configured to receive a biopsy needle therethrough, such as a septum or a rubber stopper, for placing a biological sample into the container. In some embodiments, the sample port can be configured to retain a swab or brush tool, used for obtaining tissue or fluid samples, within the headspace 308 of container 300. In some embodiments, the sample port can define an opening having a cap, lid, or other type of sealing mechanism. In some embodiments, container 300 can include a vacuum in the headspace prior to placing a biological sample therein, as will be discussed below. In various embodiments, the container can include indicia 340, such as a scoring mark, raised metering line, inked line, etc. in order to indicate to a user a desired level for filling of a biological sample into the container and thus leaving a predetermined headspace 308 volume.

The containers herein can be made from many materials, including glass, polymeric materials, metals, and the like. In some embodiments, the containers are sealed from the surrounding environment. In other embodiments, the containers are sterile on the interior.

The headspace 308 in FIG. 3 is shown as contained completely within the internal environment of container 300 and above biological sample 306. In other embodiments, such as in the case of a solid tissue sample, such as an organ biopsy, bone biopsy, or the like, the headspace can include the entire volume of gas within the container that is surrounding the biological sample, including alongside the biological sample or under the biological sample, as will be discussed further in reference to FIG. 6. It will be appreciated that the containers herein that provide a headspace can come in several shapes, sizes, and configuration, and can be customized for a particular biological sample type.

While the biological sample 306 shown in FIG. 3 is depicted as a liquid, it will be appreciated that the biological sample can include, but not be limited to, a tissue, a liquid, and/or a solid. By way of example, the biological sample can include one or more of an organ biopsy, blood, urine, bile, sweat, feces, lymph, cerebrospinal fluid, amniotic fluid, pericardial fluid, peritoneal fluid, saliva, synovial fluid, serous fluid, sebum, bone biopsy, muscle biopsy, cheek swab biopsy, or isolated cells, or the like. In other embodiments, the biological sample of a subject can include any of the above examples and can additionally include the presence of one or more pathogenic bacteria within the biological sample of a subject.

When the container 300 is devoid of a biological sample, the headspace 308 can include ambient gas, inert gas, or it can be flushed with an inert gas prior to placing a biological sample 306 into the container 300. In some embodiments, the volume of gas in the headspace can include an inert gas such as nitrogen ($N_2$) gas. In other embodiments, the volume of gas in the headspace can include, but not be limited to, the inert gases helium (He), neon (Ne), argon (Ar), krypton (Kr), or xenon (Xe). In some embodiments the container can include a vacuum in the headspace prior to placing a biological sample therein. In other embodiments, the container can include a partial vacuum in the headspace prior to placing a biological sample therein. In some embodiments, the container can include a vacuum or partial vacuum. It will be appreciated that the pressure inside the vacuum can include any pressure that is lower than standard atmospheric pressure (i.e., less than 760 mm Hg). For example, in some embodiments the pressure can be lower than 760, 750, 740, 730, 720, 710, 700, 680, 660, 640, 620, 600, 580, 550, 500, 450, 400, 350, 300, 250, 200, 150, 100, or 50 mm Hg, or can fall within a range between any of the foregoing and can be so in a steady-state or transitorily. It will be appreciated that the pressure inside the vacuum can include any pressure that is lower than the ambient pressure of the environment surrounding the container. However, in other embodiments, the pressure within the container may be equal to or higher than the ambient pressure of the local environment. For example, in some embodiments the pressure can be higher than 760, 770, 800, 850, 900, 950, 1000, 1100, 1200, 1300, 1500, 1750, 2000, 2250, 2500, 2750, 3000, 3500, 4000, 5000, or 6000 mm Hg, or can fall within a range between any of the foregoing and can be so in a steady-state or transitorily.

To optimize detection of VOCs emitted by a biological sample, the headspace volume, the biological sample volume, and the total container volume of a container can be tailored to the size and type of biological sample. In some embodiments, the volume of the headspace can be from 0.5 volume percent (vol. %) of the total container volume to about 15 vol. % of the total container volume when a biological sample is present. In other embodiments, the volume of the headspace can be from 10 vol. % to 50 vol. % of the total container volume when a biological sample is present. In yet other embodiments, the volume of the headspace can be from 75 vol. % to 95 vol. % of the total container volume when a biological sample is present The volume of the headspace can be 0.5 vol. %, 1 vol. %, 2 vol. %, 3 vol. %, 4 vol. %, 5 vol. %, 6 vol. %, 7 vol. %, 8 vol. %, 9 vol. %, 10 vol. %, 15 vol. %, 20 vol. %, 25 vol. %, 30 vol. %, 35 vol. %, 40 vol. %, 45 vol. %, 50 vol. %, 55 vol. %, 60 vol. %, 65 vol. %, 70 vol. %, 75 vol. %, 80 vol. %, 85 vol. %, 90 vol. %, 95 vol. %, or 99 vol. % of the total container volume when a biological sample is present. It will be appreciated that the volume of the headspace can include any volume percentage of the total container volume within a range, wherein any of the forgoing volume percentages can serve as the lower or upper bound of the range, provided that the lower bound of the range is a value less than the upper bound of the range.

The headspace within a container can also be customized with respect to the size of the biological sample. For example, in some embodiments, the volume of the headspace can be 50% or less than the biological sample volume. In some embodiments, the volume of the headspace can be 100% or less than the biological sample volume. In other embodiments, the volume of the headspace can be 200% or less than the biological sample volume. In yet other embodiments, the volume of the headspace can be 400% or less than the biological sample volume.

The biological sample volumes suitable for use with the containers herein can vary depending on the type and availability of the biological sample. In some embodiments, the biological sample volume can be from 1 microliter (μl) to about 1 milliliter (ml). In some embodiments, the biological sample volume can be from 1 ml to 100 ml. In other embodiments, the biological sample volume can be from 100 ml to 1 L. In various embodiments, the biological sample volume can be 0.5 μl, 1 μl, 2 μl, 3 μl, 4 μl, 5 μl, 6 μl, 7 μl, 8 μl, 9 μl, 10 μl, 20 μl, 30 μl, 40 μl, 50 μl, 60 μl, 70 μl, 80 μl, 90 μl, 100 μl, 250 μl, 500 μl, 750 μl, 1 ml, 10 ml, 25 ml, 50 ml, 75 ml, 100 ml, 250 ml, 500 ml, 750 ml, or 1 L. In yet other embodiments, the biological sample volume can be greater than 1 L.

The total container volumes suitable for the containers herein can vary depending on the type and volume of the biological sample. In some embodiments, the total container volume can be from 1 microliter (µl) to about milliliter (ml). In some embodiments, the total container volume can be from 1 ml to 100 ml. In other embodiments, the total container volume can be from 100 ml to 1 L. In various embodiments, the total container volume can be 1 µl, 2 µl, 3 µl, 4 µl, 5 µl, 6 µl, 7 µl, 8 µl, 9 µl, 10 µl, 20 µl, 30 µl, 40 µl, 50 µl, 60 µl, 70 µl, 80 µl, 90 µl, 100 µl, 250 µl, 500 µl, 750 µl, 1 ml, 10 ml, 25 ml, 50 ml, 75 ml, 100 ml, 250 ml, 500 ml, 750 ml, or 1 L. In yet other embodiments, the total container volume can be greater than 1 L.

Figure 4:
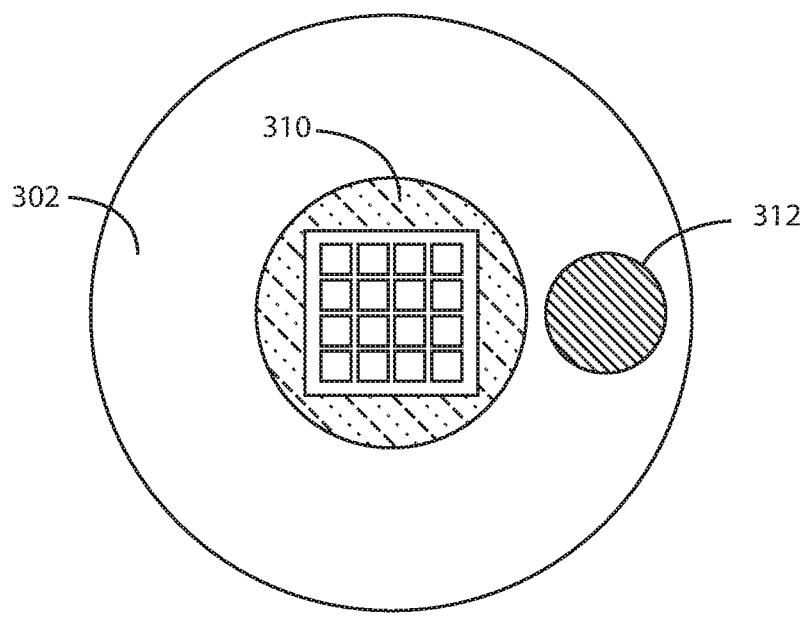
FIG. 4 is a schematic view of the container of FIG. 3 along line 4-4' in accordance with various embodiments herein.
Figure 5:
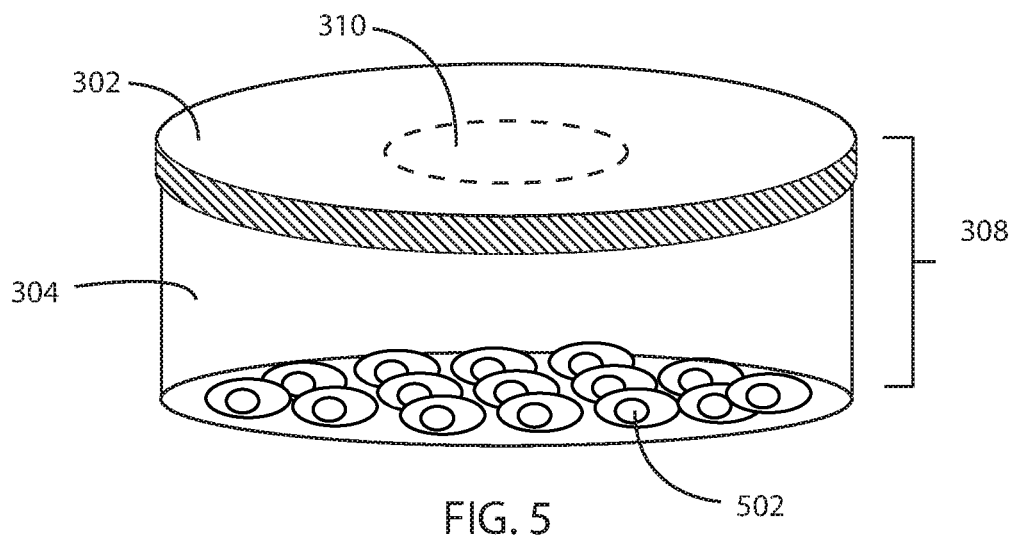
FIG. 5 is a schematic diagram of a container in accordance with various embodiments herein.

Gasses from the headspace can interface with a chemical sensor element disposed on, integrated within, or in fluid communication with the containers described herein. The container 300 shown in FIG. 3 can include a chemical sensor element 310 having a plurality of discrete graphene varactors disposed thereon. The chemical sensor element 310 can be disposed on or integrated within the lid 302 and in fluid communication with the headspace 308. When VOCs are released into the headspace by a biological sample 306, the VOCs present in the gas from the headspace 308 can interface with the plurality discrete graphene varactors to influence sensed capacitance. A schematic view of the chemical sensor element 310 of FIG. 3 along line 4-4' is shown in FIG. 4 in accordance with various embodiments herein. It will be appreciated that the chemical sensor element 310 having a plurality of discrete graphene varactors disposed thereon can come in many shapes and sizes, as will be discussed below in reference to FIGS. 13-16.

Figure 6:
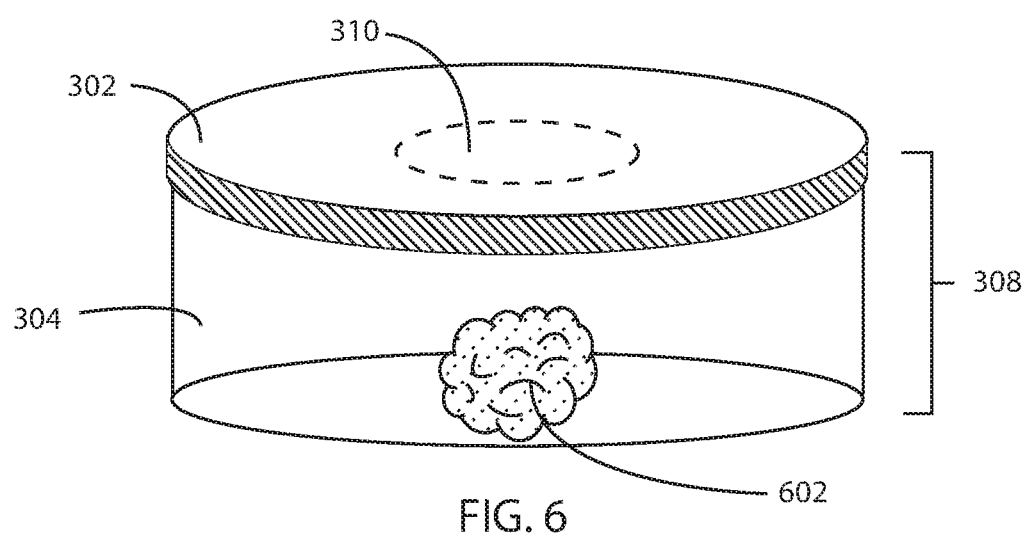
FIG. 6 is a schematic diagram of a container in accordance with various embodiments herein.

It will be appreciated that while the biological sample 306 in FIG. 3 is shown as a liquid, it can also include additional forms of biological samples, including but not limited to a tissue sample or a solid sample. By way of example, FIG. 5 includes a tissue sample 502, that can optionally be bathed in a tissue culture medium. The tissue sample 502 is shown at the base housing 304 of the container. The headspace 308 includes all of the volume of the inside of the container not occupied by the volume of the tissue sample 502, including the volume between the cells. Referring now to FIG. 6, the biological sample includes a solid sample 602 shown at the base housing 304 of the container. The headspace 308 includes the entire volume of gas above or surrounding the solid sample 602.

Figure 7:
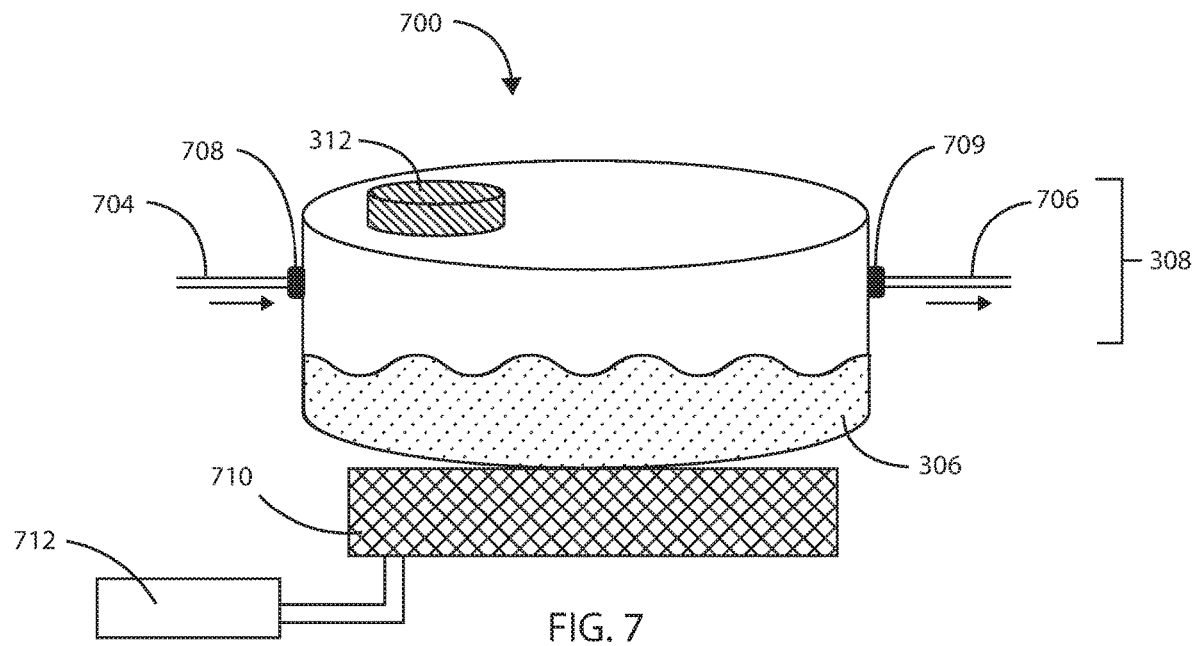
FIG. 7 is a schematic diagram of a container in accordance with various embodiments herein.

Gasses from the headspace can also interface with a chemical sensor element that is external to and in fluid communication with the containers described herein. Referring now to FIG. 7, a schematic diagram of a container 700 is shown in accordance with various embodiments herein. Container 700 can include a sample surface adapted to contain a biological sample 306 of a subject. Container 700 can include a sample port 312 for placing a biological sample into the container 700. The sample port 312 can be removably connected to the container 700 or it can be integral with the container 700. In some embodiments, sample port 312 can include a polymeric material that can be configured to receive a biopsy needle therethrough, such as a septum or a rubber stopper, for placing a biological sample into the container. In some embodiments, the sample port can be configured to retain a swab or brush tool, used for obtaining tissue or fluid samples, within the headspace 308 of container 700. In some embodiments, the sample port can define an opening having a cap, lid, or other type of sealing mechanism.

Container 700 can be in fluid communication with a chemical sensor element for direct headspace sampling. The container 700 can include a gas inlet conduit 704 and a gas outlet conduit 706, where the gas outlet conduit 706 is in fluid communication with one or more downstream chemical sensor elements. Gas inlet conduit 704 can be connected to a carrier gas supply line upstream from container 700. Gas from the headspace can be continuously drawn from the container 700 and contacted with the chemical sensor element downstream. The carrier gas can include ambient air, or it can include an inert gas such as nitrogen ($N_2$), helium (He), neon (Ne), argon (Ar), krypton (Kr), or xenon (Xe). The carrier gas can be used to drive the gas within the headspace 308 out of the container through the gas outlet conduit 706 and into contact with one or more chemical sensor elements downstream the container 700. The gas flow is depicted by the arrows in FIG. 7. The gas inlet conduit 704 and gas outlet conduit 706 can be integral to the container 700 or each can be connected to the container 700 by an air tight gasket, or gas inlet port 708 and gas outlet port 709.

In some embodiments, container 700 can be in contact with a temperature regulator 710 to maintain the temperature of the biological sample 306 at a desired temperature, such as within a physiological temperature range. In some embodiments, the temperature regulator can include a heat source that can be controlled by a thermostat 712 that can be used to keep the temperature of the biological sample constant. The temperature regulator 710 can be used to increase or decrease the temperature of the biological sample in a stepwise fashion, as will be discussed in more detail below. It will be appreciated that in some embodiments, the temperature regulator 710 can alternatively include a cooling apparatus to remove heat and cool the temperature of the biological sample below a desired temperature, such as below a physiological temperature range.

Figure 8:
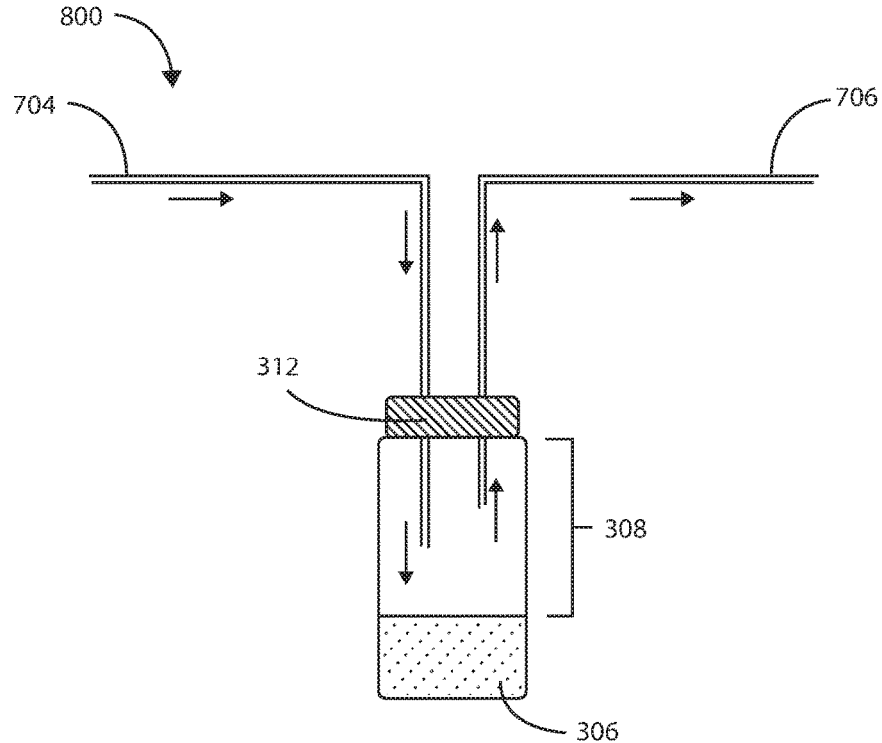
FIG. 8 is a schematic diagram of a container in accordance with various embodiments herein.

The biological samples suitable for use herein may include those that are limited in size due to sample availability. When the size of a biological sample is limited, the container size can be reduced to accommodate the small sample size. Referring now to FIG. 8, a schematic diagram of a container 800 is shown in accordance with various embodiments herein. Container 800 can include a housing adapted to contain a biological sample 306 of a subject. Container 800 can include a sample port 312 for placing a biological sample into the container 800. The sample port 312 can be removably connected to the container 800 or it can be integral with the container 800. In some embodiments, sample port 312 can be formed of a polymeric material that can be configured to receive a biopsy needle therethrough for placing a biological sample into the container.

Container 800 can be in fluid communication with a chemical sensor element for direct headspace sampling. The container 800 can include a gas inlet conduit 704 and a gas outlet conduit 706, where the gas outlet conduit 706 is in fluid communication with one or more downstream chemical sensor elements. Gas inlet conduit 704 can be connected to a carrier gas supply line upstream from container 800. Gas from the headspace can be continuously drawn from the container 800 and contacted with the chemical sensor element downstream. The carrier gas can include ambient air, or it can include an inert gas such as nitrogen ($N_2$), helium (He), neon (Ne), argon (Ar), krypton (Kr), or xenon (Xe). In some embodiments, the container 800 can include a vacuum prior to placing a biological sample inside or it can be at ambient pressure or higher. The carrier gas can be used to drive the gas within the headspace 308 out of the container through the gas outlet conduit 706 and into contact with one or more downstream chemical sensor elements. The gas flow is depicted by the arrows in FIG. 8. The gas inlet conduit 704 and gas outlet conduit 706 can be introduced into the container 800 through the sample port 312.

In some embodiments, biological samples can be removed from a subject using a needle and syringe. To minimize handling of the biological sample, the syringe or other sampling device can be configured as a container suitable for use in the embodiments herein. By way of example, referring now to FIG. 9 a schematic diagram of a container 900 is shown in accordance with various embodiments herein. Container 900 includes a syringe barrel 902, a syringe plunger 904, a needle 906, and a chemical sensor element 310. In some embodiments, the container 900 can include a needle coupling 908 disposed between the syringe barrel 902 and needle 906. The needle 906 can be inserted into a subject to remove a biological sample 306. The biological sample 306 can be drawn through the needle 906 and into the syringe barrel 902.

The container 900 can be configured to include a chemical sensor element 310 to analyze the VOC emissions of a biological sample 306. In this embodiment, the syringe plunger 904 includes a chemical sensor element on the face of the syringe plunger 904 disposed within the headspace 308 of syringe barrel 902. Thus, in some embodiments, analysis of the biological sample 306 can occur immediately after removal from a subject. In other embodiments, the biological sample 306 can be allowed to incubate within the syringe barrel 902 for a period of time to allow for emission of VOCs into the headspace 308 to equilibrate with the biological sample 306. In some embodiments, the syringe plunger 904 can be adjusted to increase or decrease the volume of gas in headspace 308.

Figure 9:
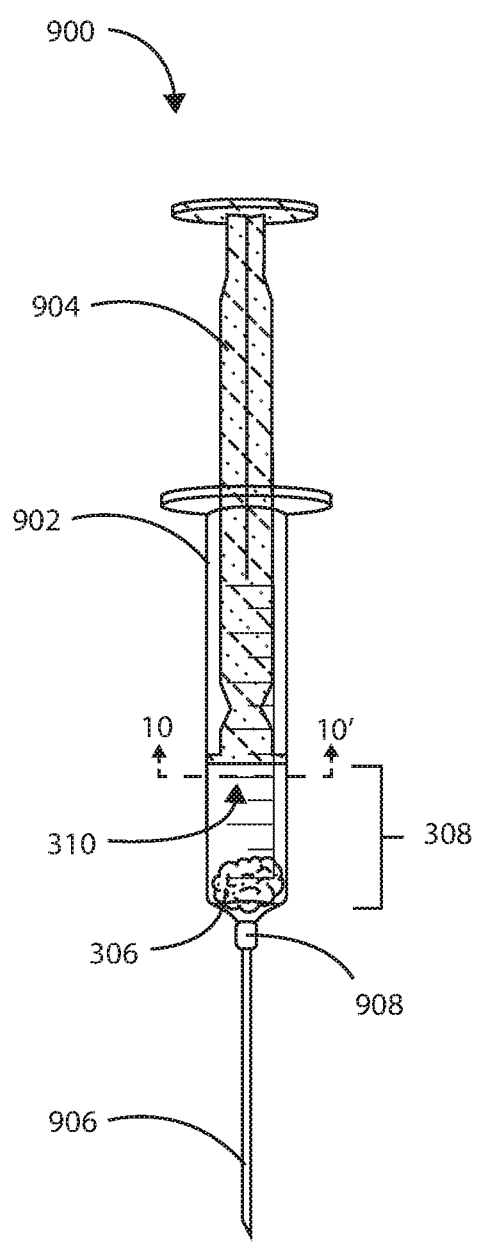
FIG. 9 is a schematic diagram of a container in accordance with various embodiments herein.
Figure 10:
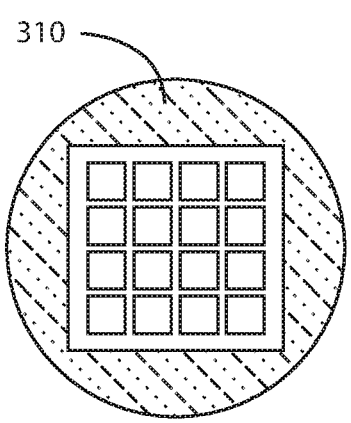
FIG. 10 is a schematic view of the container of FIG. 9 along line 9-9' in accordance with various embodiments herein.
Figure 11:
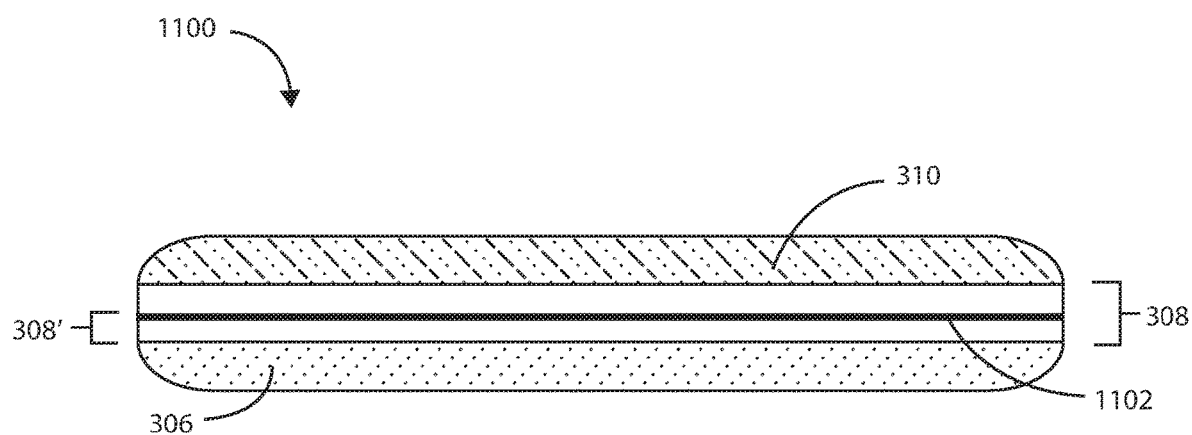
FIG. 11 is a schematic diagram of a container in accordance with various embodiments herein.

A schematic view of the chemical sensor element 310 disposed on the interior face of the syringe plunger 904 of FIG. 9 along line 10-10' is shown in FIG. 10 in accordance with various embodiments herein. It will be appreciated that the chemical sensor element 310 having a plurality of discrete graphene varactors disposed thereon can come in many shapes and sizes, as will be discussed below in reference to FIGS. 13-16.

It will be appreciated that in some embodiments, a biological sample can be placed into a container that is temporarily separate or isolated from the chemical sensor element. Separation of the biological sample from the chemical sensor element for a period of time can allow the VOCs emitted by the biological sample 306 to equilibrate into the headspace. By way of example, referring now to FIG. 11, a schematic diagram of a container 1100 is shown in accordance with various embodiments herein. Container 1100 includes a biological sample 306, a chemical sensor element 310, and a partition 1102, such as a film, a foil, a movable wall, a sliding member, a mechanical iris, and the like, separating the biological sample 306 from the chemical sensor element 310. The partition 1102 creates a temporary headspace 308' and is configured to be opened or closed during use. When the partition 1102 is opened, it allows for the gas in the headspace to diffuse into the full headspace 308 and come into contact with the chemical sensor element 310. In some embodiments, the partition 1102 can be used when incubating a biological sample 306 for a period of time before the gas from the headspace is contacted with the chemical sensor element 310.

Aspects of exemplary chemical sensor elements can be found in U.S. Patent Application Publication No. 2016/0109440A1, the content of which is herein incorporated by reference in its entirety.

Figure 12:
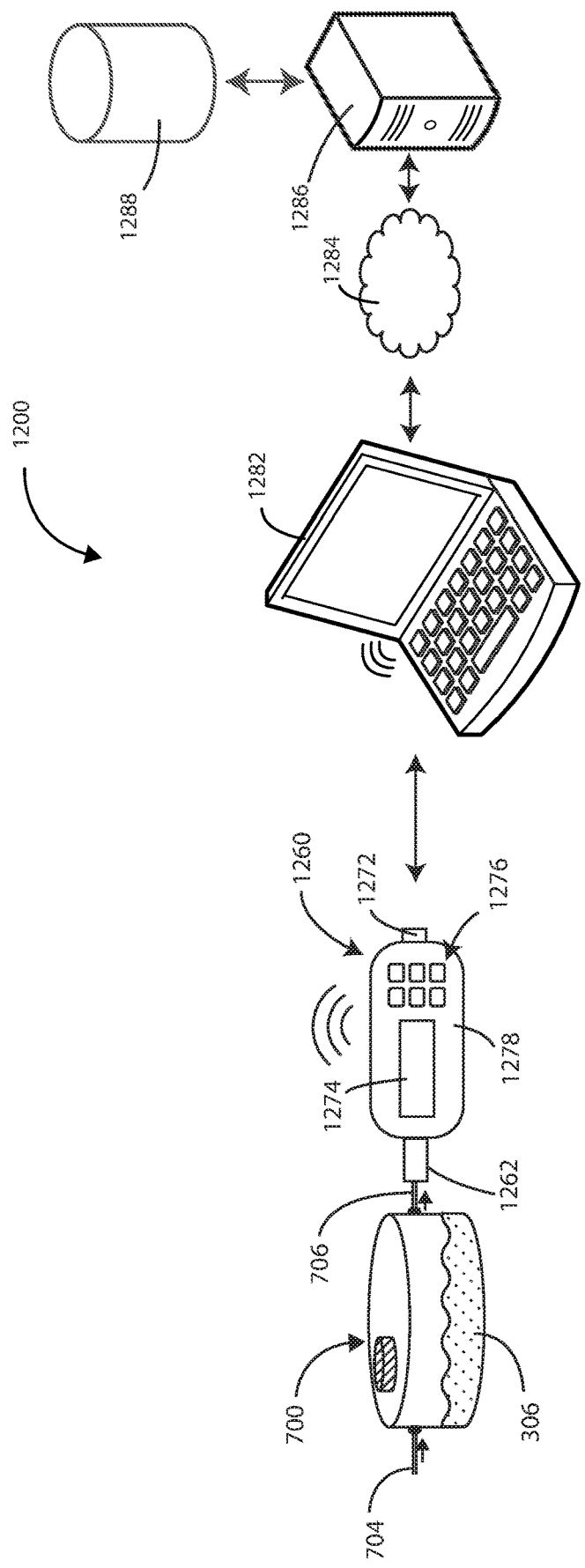
FIG. 12 is a schematic view of various components of a system in accordance with various embodiments herein.

The containers herein can interface with a system for sensing a capacitance in the plurality of graphene varactors. Referring now to FIG. 12, a schematic view is shown of components of a system 1200 in accordance with various embodiments herein. The system 1200 can include a container 700 and a sensing device 1260 for sensing volatile organic compounds in a biological sample 306 of a subject. In the embodiment in FIG. 12, the sensing device 1260 and system 1200 is in a hand-held format that can be used in the field. It will be appreciated, however, that many other formats for the sensing device 1260 and system 1200 are contemplated herein.

While container 700 described in FIG. 7 is shown as an exemplary container in system 1200, it will be appreciated that any of the containers described in the various embodiments herein can be used in system 1200. The sensing device 1260 can include a housing 1278. The sensing device 1260 can include an air intake port 1262 that can be can be in fluid communication with the gas outlet conduit 706 of container 700. The sensing device 1260 can be configured to actively draw a gas into housing 1278 or it can be configured to receive a gas passively from a carrier gas supply line upstream from container 700. In some embodiments, the biological sample 306 can be incubated for a period of time before the gas from the headspace drawn into sensing device 1260. In some embodiments, the biological sample can be incubated for 5 minutes, 10 minutes, 30 minutes, 1 hour, 1 day, 1 week, or more.

The sensing device 1260 can also include a display screen 1274 and a user input device 1276, such as a keyboard. The sensing device 1260 can also include a gas outflow port 1272. Aspects of sensing systems and devices are described in U.S. Patent Application Publication No. 2016/0109440, the content of which is herein incorporated by reference. While FIG. 12 shows a sensing device 1260 adapted to receive gas from a headspace within a container, it will be appreciated that other types of gas sampling systems can also be used herein. For example, gas sampling devices for use with catheters and endoscopy systems can also be used. An exemplary gas sampling device in the context of a catheter or endoscopy device is described in U.S. Patent Application Publication No. 2017/0360337A1, the content of which is herein incorporated by reference.

In some embodiments, the system 1200 can include a local computing device 1282 that can include a microprocessor, input and output circuits, input devices, a visual display, a user interface, and the like. In some embodiments, the sensing device 1260 can communicate with the local computing device 1282 in order to exchange data between the sensing device 1260 and the local computing device 1282. The local computing device 1282 can be configured to perform various processing steps with the data received from the sensing device 1260, including, but not limited to, calculating various parameters described herein. However, it should be appreciated that in some embodiments the features associated with the local computing device 1282 can be integrated into the sensing device 1260. In some embodiments, the local computing device 1282 can be a laptop computer, a desktop computer, a server (real or virtual), a purpose dedicated computer device, or a portable computing device (including, but not limited to, a mobile phone, tablet, wearable device, etc.).

The local computing device 1282 and/or the sensing device 1260 can communicate with computing devices in remote locations through a data network 1284, such as the Internet or another network for the exchange of data as packets, frames, or otherwise.

In some embodiments, the system 1200 can also include a computing device such as a server 1286 (real or virtual). In some embodiments, the server 1286 can be located remotely from the sensing device 1260. The server 1286 can be in data communication with a database 1288. The database 1288 can be used to store various subject information, such as that described herein. In some embodiments, the database can specifically include an electronic medical database containing data regarding the health status of a subject, patterns of data associated with various conditions (such as that generated from machine learning analysis of large sets of subject data), demographic data and the like. In some embodiments, the database 1288 and/or server 1286, or a combination thereof, can store the data generated by the chemical sensor(s) as well as data output generated by machine learning analysis.

Figure 13:
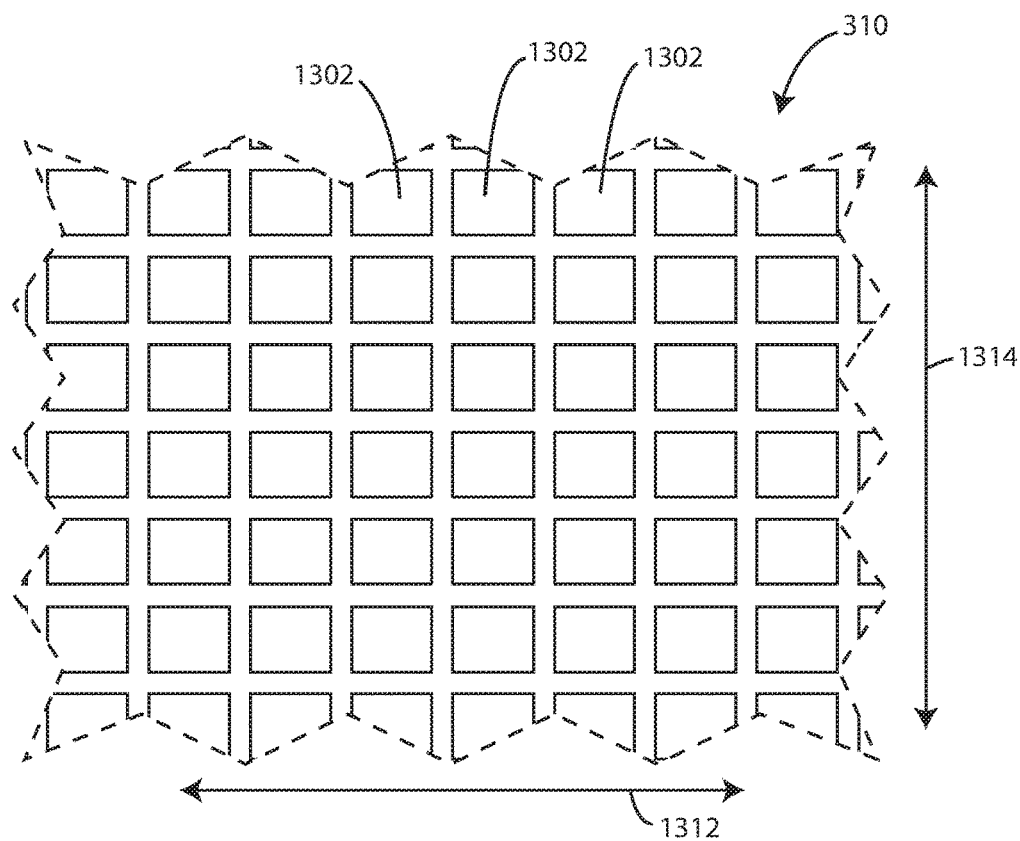
FIG. 13 is a schematic diagram of a portion of a chemical sensor element in accordance with various embodiments herein.

Referring now to FIG. 13, a schematic diagram of a portion of a chemical sensor element 310 is shown in accordance with various embodiments herein. A plurality of discrete graphene varactors 1302 can be disposed on the chemical sensor element 310 in an array. In some embodiments, a chemical sensor element can include a plurality of discrete graphene varactors configured in an array. In some embodiments, the plurality of discrete graphene varactors can be identical, while in other embodiments the plurality of discrete graphene varactors can be different from one another. The discrete graphene varactors herein can be as described in more detail in U.S. Pat. No. 9,513,244, which is herein incorporated by reference in its entirety.

In some embodiments, the discrete graphene varactors can be heterogeneous in that they are different (in groups or as individual discrete graphene varactors) from one another in terms of their binding behavior or specificity with regard a particular analyte. In some embodiments, some discrete graphene varactors can be duplicated for validation purposes but are otherwise heterogeneous from other discrete graphene varactors. Yet in other embodiments, the discrete graphene varactors can be homogeneous. While the discrete graphene varactors 1302 of FIG. 13 are shown as boxes organized into a grid, it will be appreciated that the discrete graphene varactors can take on many different shapes (including, but not limited to, various polygons, circles, ovals, irregular shapes, and the like) and, in turn, the groups of discrete graphene varactors can be arranged into many different patterns (including, but not limited to, star patterns, zig-zag patterns, radial patterns, symbolic patterns, and the like).

In some embodiments, the order of specific discrete graphene varactors 1302 across the length 1312 and width 1314 of the measurement zone can be substantially random. In other embodiments, the order can be specific. For example, in some embodiments, a measurement zone can be ordered so that the specific discrete graphene varactors 1302 for analytes having a lower molecular weight are located farther away from the incoming gas flow relative to specific discrete graphene varactors 1302 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete graphene varactors.

The number of discrete graphene varactors can be from about 1 to about 100,000. In some embodiments, the number of discrete graphene varactors can be from about 1 to about 10,000. In some embodiments, the number of discrete graphene varactors can be from about 1 to about 1,000. In some embodiments, the number of discrete graphene varactors can be from about 2 to about 500. In some embodiments, the number of discrete graphene varactors can be from about 10 to about 500. In some embodiments, the number of discrete graphene varactors can be from about 50 to about 500. In some embodiments, the number of discrete graphene varactors can be from about 1 to about 250. In some embodiments, the number of discrete graphene varactors can be from about 1 to about 50.

In some embodiments, each of the discrete graphene varactors suitable for use herein can include at least a portion of one or more electrical circuits. By way of example, in some embodiments, each of the discrete graphene varactors can include all or a portion of one or more passive electrical circuits. In some embodiments, the graphene varactors can be formed such that they are integrated directly on an electronic circuit. In some embodiments, the graphene varactors can be formed such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a biological sample. Many different types of circuits can be used to gather data from chemical sensor elements and will be discussed below in reference to FIGS. 15 and 16.

Figure 14:
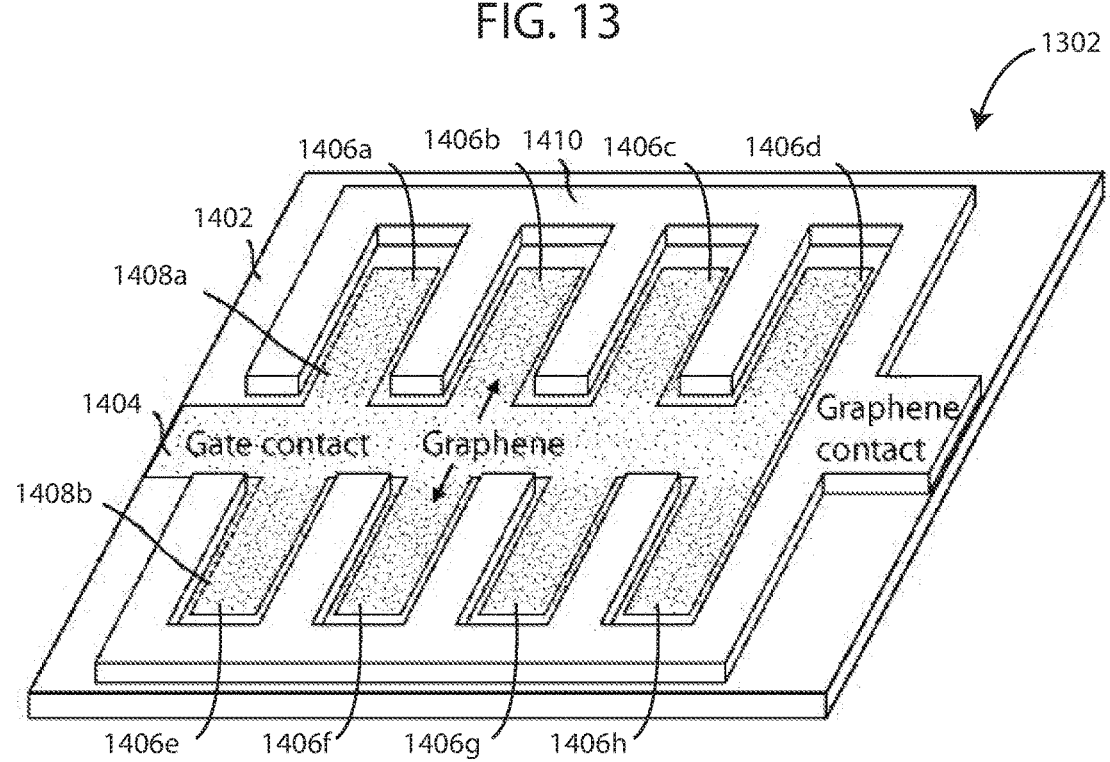
FIG. 14 is a schematic perspective view of a discrete graphene varactor in accordance with various embodiments herein.

In some embodiments, the discrete graphene varactors embodied herein can include graphene-based variable capacitors (or graphene varactors). Referring now to FIG. 14, a schematic view of a discrete graphene varactor 1302 is shown in accordance with the embodiments herein. It will be appreciated that discrete graphene varactors can be prepared in various ways with various geometries, and that the discrete graphene varactor shown in FIG. 14 is just one example in accordance with the embodiments herein.

Discrete graphene varactor 1302 can include an insulator layer 1402, a gate electrode 1404 (or "gate contact"), a dielectric layer (not shown in FIG. 14), one or more graphene layers, such as graphene layers 1408a and 1408b, and a contact electrode 1410 (or "graphene contact"). In some embodiments, the graphene layer(s) 1408a-b can be contiguous, while in other embodiments the graphene layer(s) 1408a-b can be non-contiguous. Gate electrode 1404 can be deposited within one or more depressions formed in insulator layer 1402. Insulator layer 1402 can be formed from an insulative material such as silicon dioxide, formed on a silicon substrate (wafer), and the like. Gate electrode 1404 can be formed by an electrically conductive material such as chromium, copper, gold, silver, tungsten, aluminum, titanium, palladium, platinum, iridium, and any combinations or alloys thereof, which can be deposited on top of or embedded within the insulator layer 1402. The dielectric layer can be disposed on a surface of the insulator layer 1402 and the gate electrode 1404. The graphene layer(s) 1408a-b can be disposed on the dielectric layer.

Discrete graphene varactor 1302 includes eight gate electrode fingers 1406a-1406h. It will be appreciated that while discrete graphene varactor 1302 shows eight gate electrode fingers 1406a-1406h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Discrete graphene varactor 1302 can include one or more contact electrodes 1410 disposed on portions of the graphene layers 1408a and 1408b. Contact electrode 1410 can be formed from an electrically conductive material such as chromium, copper, gold, silver, tungsten, aluminum, titanium, palladium, platinum, iridium, and any combinations or alloys thereof. Further aspects of exemplary graphene varactors can be found in U.S. Pat. No. 9,513,244, the content of which is herein incorporated by reference in its entirety.

The capacitance of the graphene varactors can be measured by delivering an excitation current at a particular voltage and/or over a range of voltages. Measuring the capacitance provides data that reflects the binding status of analytes to the graphene varactor(s). Various measurement circuitry can be used to measure the capacitance of the graphene varactor(s).

Figure 15:
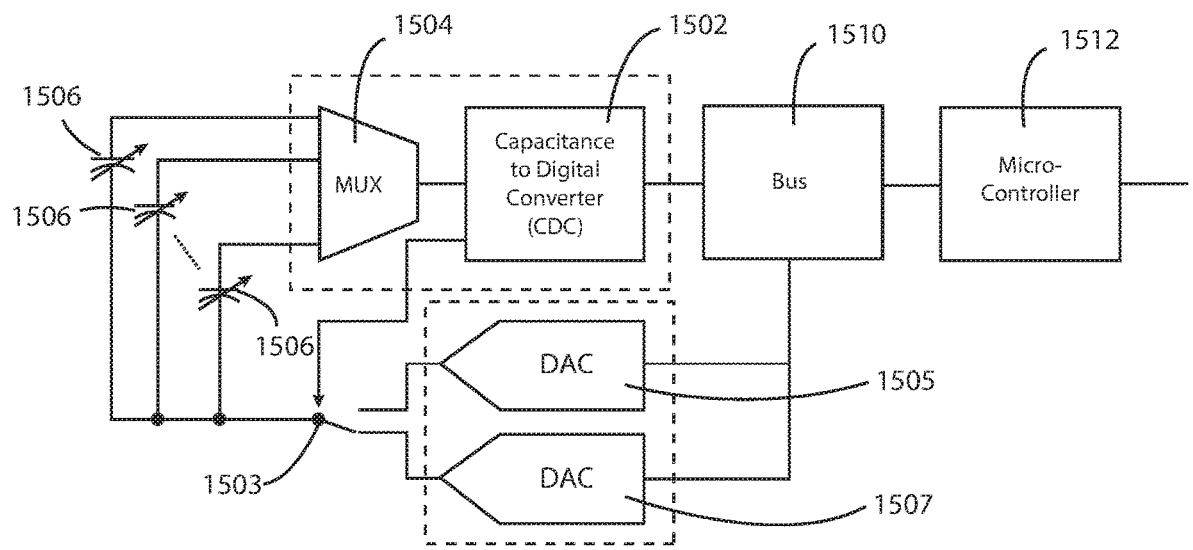
FIG. 15 is a schematic diagram of circuitry to measure the capacitance of a plurality of discrete graphene varactors in accordance with various embodiments herein.

Referring now to FIG. 15, a schematic diagram is shown of circuitry to measure the capacitance of a plurality of graphene sensors in accordance with various embodiments herein. The circuitry can include a capacitance to digital converter (CDC) 1502 in electrical communication with a multiplexor 1504. The multiplexor 1504 can provide selective electrical communication with a plurality of graphene varactors 1506. The connection to the other side of the graphene varactors 1506 can be controlled by a switch 1503 (as controlled by the CDC) and can provide selective electrical communication with a first digital to analog converter (DAC) 1505 and a second digital to analog converter (DAC) 1507. The other side of the DACs 1505, 1507 can be connected to a bus device 1510, or in some cases, the CDC 1502. The circuitry can further include a microcontroller 1512, which will be discussed in more detail below.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching. Many different ranges of DC bias voltages can be used. In some embodiments, the range of DC bias voltages can be from −3 V to 3 V, or from −1 V to 1 V, or from −0.5 V to 0.5 V.

Many different aspects can be calculated based on the capacitance data. For example, aspects that can be calculated include maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value, voltage at minimum capacitance (Dirac point), change in voltage at minimum capacitance, maximum capacitance, change in maximum capacitance, ratio of maximum capacitance to minimum capacitance, response time constants, and ratios of any of the foregoing between different graphene sensors and particularly between different graphene sensors having specificity for different analytes.

The above calculated aspects can be used for various diagnostic purposes. In some cases, the above calculated aspects can be indicative of the identity and/or concentrations of specific volatile organic components of a gas sample. As such, each of the calculated values above can serve as a distinct piece of data that forms part of a pattern for a given subject and/or given gas sample. As also described elsewhere herein, the pattern can then be matched against preexisting patterns, or patterns identified in real-time, derived from large stored data sets through techniques such as machine learning or other techniques, wherein such patterns are determined to be characteristic of various conditions or disease states. The above calculated aspects can also be put to other purposes, diagnostic and otherwise.

In some embodiments, calculations such as those described above can be performed by a controller circuit. The controller circuit can be configured to receive an electrical signal reflecting the capacitance of the graphene varactors. In some embodiments, the controller circuit can include a microcontroller to perform these calculations. In some embodiments, the controller circuit can include a microprocessor in electrical communication with the measurement circuit. The microprocessor system can include components such as an address bus, a data bus, a control bus, a clock, a CPU, a processing device, an address decoder, RAM, ROM and the like. In some embodiments, the controller circuit can include a calculation circuit (such as an application specific integrated circuit—ASIC) in electrical communication with the measurement circuit.

In addition, in some embodiments, the system can include a nonvolatile memory where sensitivity calibration information for the particular sensor is stored. By way of example, the sensor could be tested in a production facility, where its sensitivity to various analytes such as VOC's can be determined and then stored on an EPROM or similar component. In addition, or alternatively, sensitivity calibration information can be stored in a central database and referenced with a sensor serial number when subject data is sent to a central location for analysis and diagnosis. These components can be included with any of the pieces of hardware described herein.

In some embodiments herein, components can be configured to communicate over a network, such as the internet or a similar network. In various embodiments, a central storage and data processing facility can be included. In some embodiments, data gathered from sensors in the presence of the subject (local) can be sent to the central processing facility (remote) via the internet or a similar network, and the pattern from the particular subject being evaluated can be compared to those of thousands or millions of other subjects, many of whom have been previously diagnosed with various conditions and wherein such condition data has been stored. Pattern matching algorithms can be used to find other subjects or classes of subjects (for example disease or condition specific classes) to which the current subject's pattern is most similar. Each class of subjects can include a predetermined likelihood of having a given condition or disease state. In this manner, after pattern matching a likelihood of having a given condition or disease state can be provided back across the data network to the facility where the subject is currently located.

In some embodiments, circuitry can include active and passive sensing circuits. Such circuitry can implement wired (direct electrical contact) or wireless sensing techniques.

Figure 16:
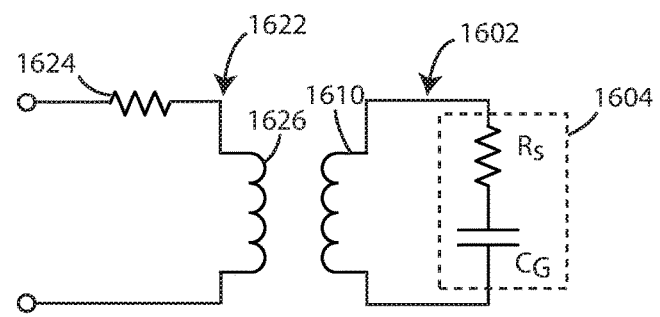
FIG. 16 is a schematic diagram of a passive sensor circuit and a portion of a reading circuit is shown in accordance with various embodiments herein.

Referring now to FIG. 16, a schematic diagram of a passive sensor circuit 1602 and a portion of a reading circuit 1622 is shown in accordance with various aspects herein. In some embodiments, the passive sensor circuit 1602 can include a metal-oxide-graphene varactor 1604 (wherein RS represents the series resistance and CG represents the varactor capacitor) coupled to an inductor 1610. In some embodiments, the reading circuit 1622 can include a reading coil having a resistance 1624 and an inductance 1626. However, it will be appreciated that the circuits shown in FIGS. 15 and 16 are merely exemplary approaches. Many different approaches are contemplated herein.

Figure 17:
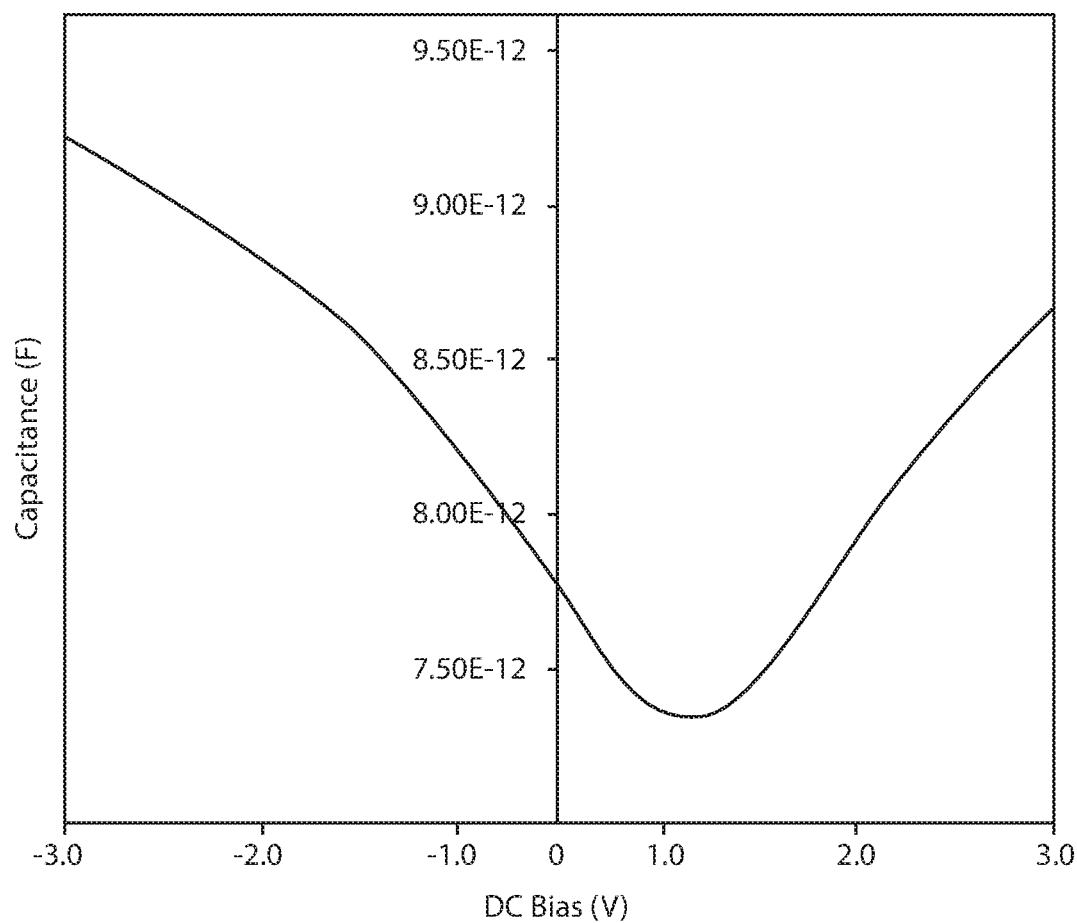
FIG. 17 is a graph showing capacitance versus DC bias voltage for a discrete graphene varactor in accordance with various embodiments herein.

Referring now to FIG. 17 an exemplary graph showing capacitance versus DC bias voltage for a graphene varactor is shown in accordance with various embodiments herein. A capacitance to voltage curve like that shown in FIG. 17 can be established by measuring capacitance over a range of bias voltages while exposing the chemical sensor to the gas emitted from a biological sample of a subject using circuits such as those described in FIGS. 15 and 16. In some embodiments, the range of bias voltages can include from −3 V to 3 V. In some embodiments, the range of DC bias voltages can be from −2 V to 2 V, or from −1.5 V to 1.5 V, or from −1 V to 1 V, or from −0.5 V to 0.5 V.

Biological Sample Handling

It will be appreciated that various biological sample collection, processing, and storage techniques can be employed when removing the biological sample from a subject in accordance with the embodiments herein. Biological samples can be removed from a subject using invasive or non-invasive collection methods. The collection methods can include minimally invasive sample collection from the subject, such as in the case of urine, feces, saliva, or buccal swab, blood draw, and the like. In some embodiments, collection methods can include a tissue biopsy from surgery, autopsy, transplant, and the like.

In some embodiments, the biological sample is minimally processed and in other embodiments the biological sample is not processed at all. In some embodiments, such as for a blood sample or a tissue sample, cells from the biological sample can be removed from extracellular matrix material or from within various blood fractions, including but not limited to serum, plasma, red blood cells, white blood cells, etc.

Once a biological sample has been obtained from a subject and placed into a container, as described elsewhere herein, the biological sample can be stored for future use or it can be used immediately. In some embodiments, the biological sample can be incubated as is, or in a tissue culture medium or cell culture medium. During incubation, the biological sample can be heated with a heat source to maintain the sample within a given temperature range. In some embodiments, the temperature range can include a physiological temperature range, such as 35 degrees Celsius (° C.) to 39° C. While in some embodiments the biological sample can be maintained at physiological temperature, in other embodiments the biological sample can be maintained at temperatures outside the physiological range. For example, the biological sample can be maintained at a temperature from about 10° C. to about 30° C. In other embodiments, the biological sample can be maintained at a temperature from 25° C. to 40° C. In other embodiments, the biological sample can be maintained at a temperature from 40° C. to 50° C.

Figure 18:
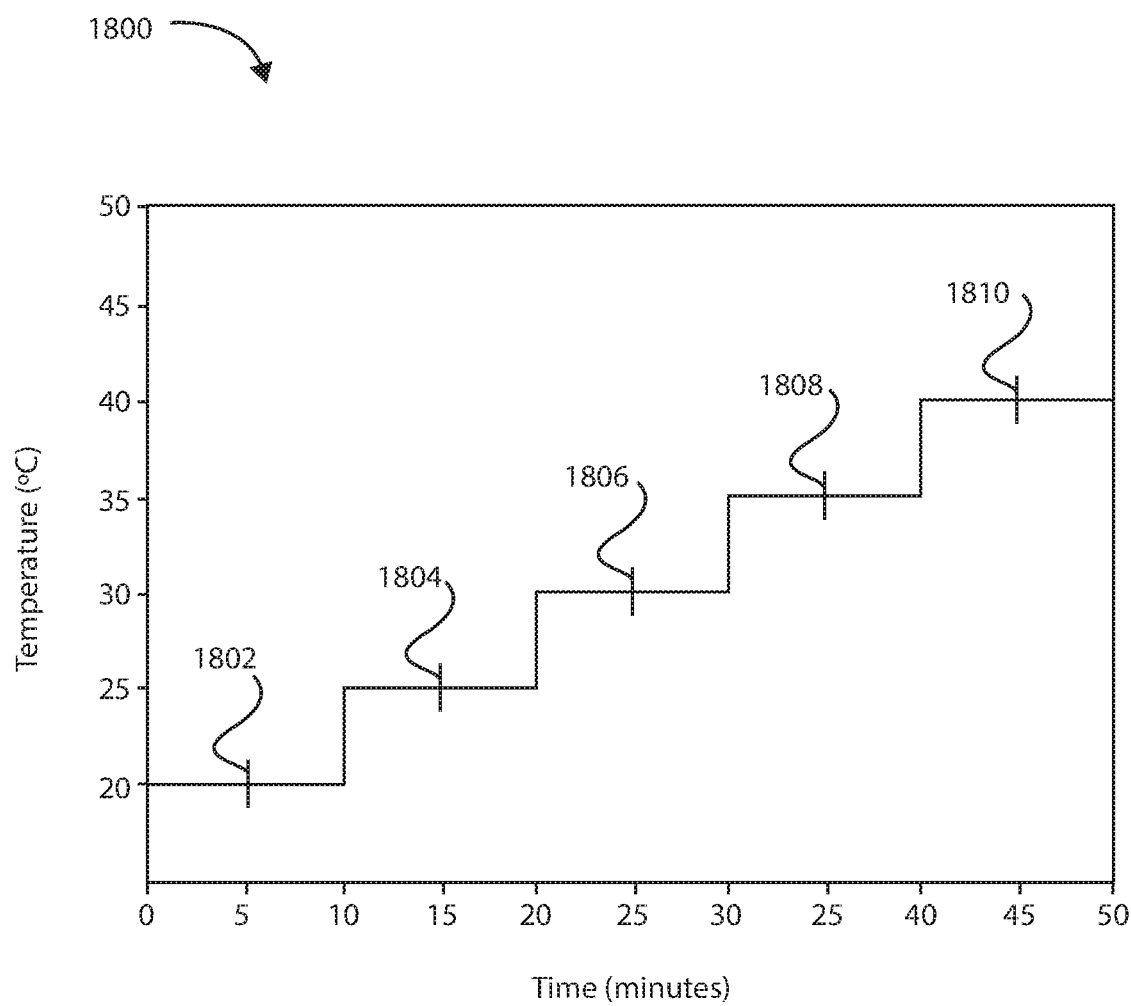
FIG. 18 is a graph of temperature versus time for sampling a headspace in accordance with various embodiments herein.

In some embodiments, the temperature for incubation of the biological sample can be increased in a stepwise fashion over a given time period. By way of example, referring now to FIG. 18, a graph 1800 of temperature versus time for sampling a headspace is shown in accordance with various embodiments herein. The biological sample can be incubated within a chosen temperature range and a chosen time period. One example for incubating a biological sample in a stepwise fashion over a given time is shown in FIG. 18, where the temperature is increased by 5° C. every ten minutes, going from 20° C. to 40° C. over a 45-minute time period. At time points 1802, 1804, 1806, 1808, and 1810, the gas from the headspace can be contacted with a chemical sensor element. The emission of VOCs can influence the capacitance of the discrete graphene varactors over the time and temperature conditions selected. The capacitance of the discrete graphene varactors can be sensed and stored to obtain a sample data set, which can be used to determine one or more preestablished disease state classifications and can be used to identify a therapy to treat a subject based on the disease state classification.

In some embodiments, the biological sample can be mechanically agitated during an incubation, prior to, or during a time when the gas from the headspace is contacting the chemical sensor element. In other embodiments, the partial pressure of the headspace can be increased to allow for an increase in the concentration of emitted VOCs into the headspace.

Additional Embodiments

Figure 19:
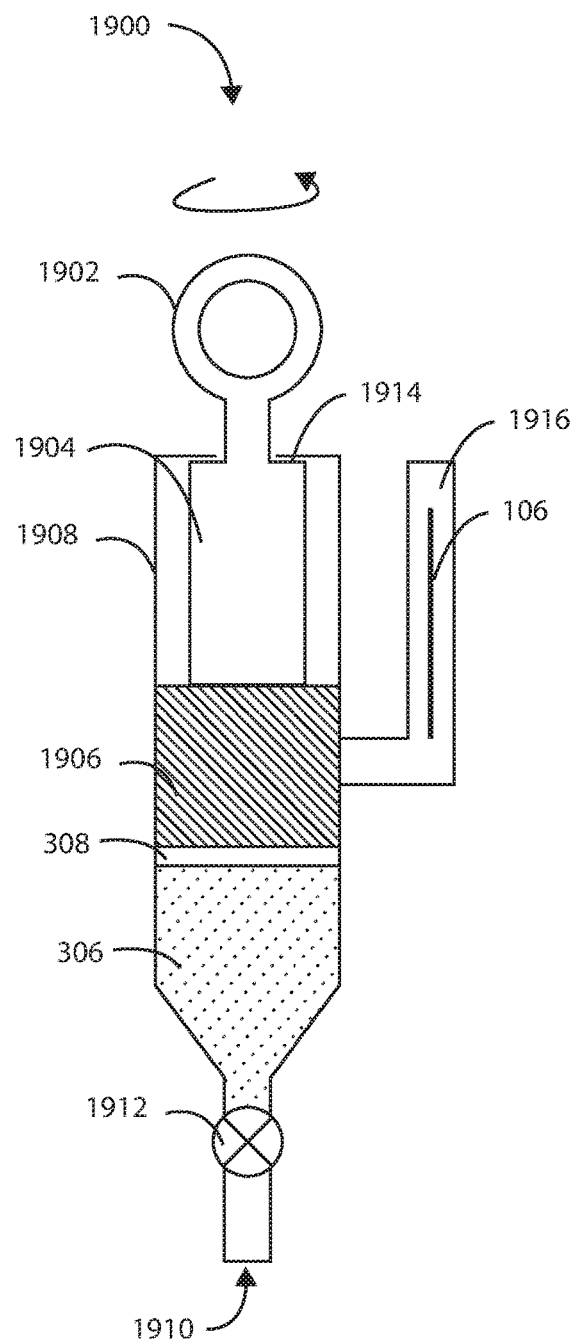
FIG. 19 is a schematic diagram of a container in accordance with various embodiments herein.
Figure 20:
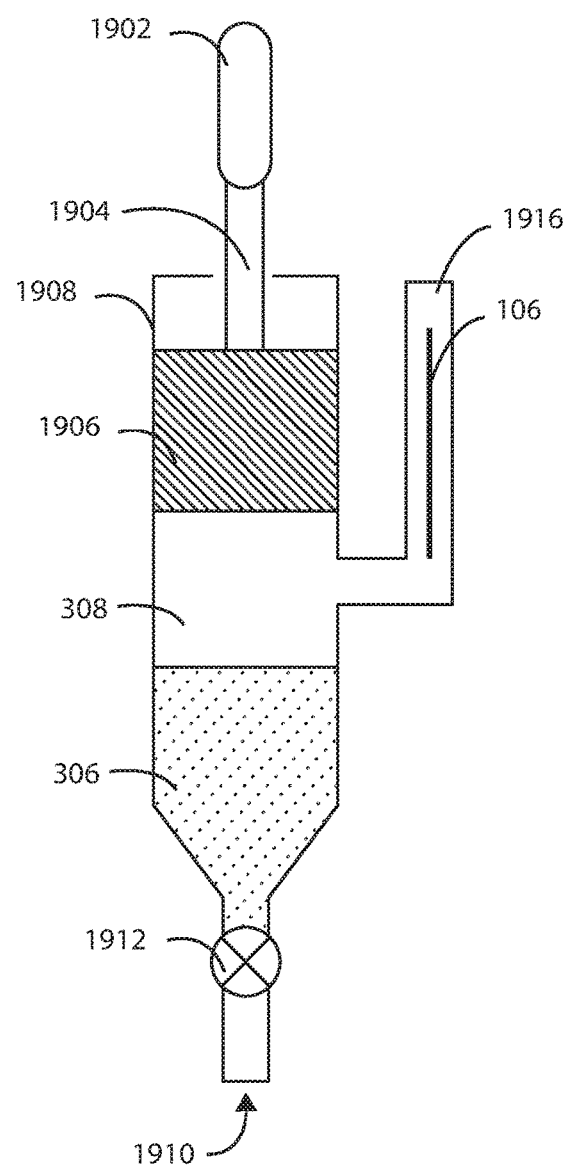
FIG. 20 is a schematic diagram of a container in accordance with various embodiments herein.

Additional embodiments of containers suitable for use with biological samples herein will be discussed in reference to FIGS. 19-22. Referring now to FIGS. 19 and 20, schematic diagrams of a container 1900 are shown in accordance with various embodiments herein. Container 1900 includes a movable sealing member such as plunger 1902. Plunger 1902 has a shaft portion 1904 and a stopper portion 1906. The plunger 1902 can include one or more shoulder portions 1914 that act as a first stop point to prevent plunger travel beyond a predetermined volume. While not shown, plunger 1902 can include additional second, third, fourth, etc. shoulder portions to provide additional stop points. Container 1900 includes a vessel body 1908 and a sample port 1910. Sample port 1910 can be configured to draw a biological sample 306 into the vessel body 1908. Sample port 1910 can be opened or closed to the external environment using a valve 1912. In some embodiments sample port 1910 includes a blunt opening. In other examples, sample port 1910 can be tapered to form a needle-like opening. It will be appreciated that while the movable sealing member is shown in FIGS. 19-22 as a plunger, various other movable sealing members can be used, such as a movable wall, a film, a foil, and the like.

The container 1900 includes a sensor element chamber 1916 in fluid communication with the interior of the vessel body 1908 and sealed from an external environment. The sensor element chamber 1916 includes a chemical sensor element 106 disposed within an inert environment. The inert environment within sensor element chamber 1916 can include an inert gas such as nitrogen ($N_2$) gas. In other embodiments, the inert environment within sensor element chamber 1916 can include, but not be limited to, the inert gases helium (He), neon (Ne), argon (Ar), krypton (Kr), or xenon (Xe). The chemical sensor element 106 can include a plurality of discrete graphene varactors as discussed elsewhere herein. In some embodiments, the sensor element chamber 1916 is integral with the vessel body 1908. In other embodiments, the sensor element chamber 1916 is removably attached to the vessel body 1908. In some embodiments, the sensor element chamber 1916 is under a vacuum.

Container 1900 can be used to draw a biological sample into the vessel body 1908. A biological sample 306 can be drawn into the vessel body 1908 of container 1900 through sample port 1910 by pulling plunger 1902 out of vessel body 1908 into a first configuration as shown in FIG. 19. The valve 1912 can be turned to a closed position to prevent backflow of biological sample 306 from vessel body 1908. The stopper portion 1906 of plunger 1902 can be positioned such that it maintains a seal over the sensor element chamber 1916 to block the fluid communication flow path between the vessel body 1908 and the sensor element chamber 1916. In some embodiments there may be a volume of gas in a headspace 308 over the biological sample 306, while in other embodiments there will be no volume of gas in a headspace 308 over the biological sample 306. In some embodiments, the biological sample includes a liquid. In other embodiments, the biological sample can include a solid. In yet other embodiments, the biological sample in includes a slurry of a solid and a liquid.

Referring now to FIG. 20, a schematic diagram of a container 1900 with the plunger 1902 in a second configuration is shown in accordance with various embodiments herein. It will be appreciated that plunger 1902 of FIG. 20 is shown rotated 90 degrees with respect to the plunger 1902 of FIG. 19. However, it will be appreciated that the plunger 1902 can be rotated freely from 0 degrees to 360 degrees about its longitudinal axis. Rotation of plunger 1902 can allow it to be pulled further out of the vessel body 1908 beyond a first stop point to an additional stop point. The action of pulling the plunger 1902 further out of the vessel body 1908 creates a vacuum within headspace 308 over biological sample 306. In some embodiments, a counterforce can be applied to plunger 1902 to keep the volume within headspace 308 constant.

The action of pulling the plunger 1902 out of the vessel body 1908 causes a drop in the pressure over the biological sample 306, which provides a driving force for the vaporization of the volatile organic compounds (VOCs) out of the biological sample 306 and into the headspace 308. Pulling the plunger 1902 out of the vessel body additionally unblocks the fluid communication flow path between the vessel body 1908 and the sensor element chamber 1916, thus exposing the chemical sensor element 106 to a volume of gas within headspace 308, including VOCs.

Figure 21:
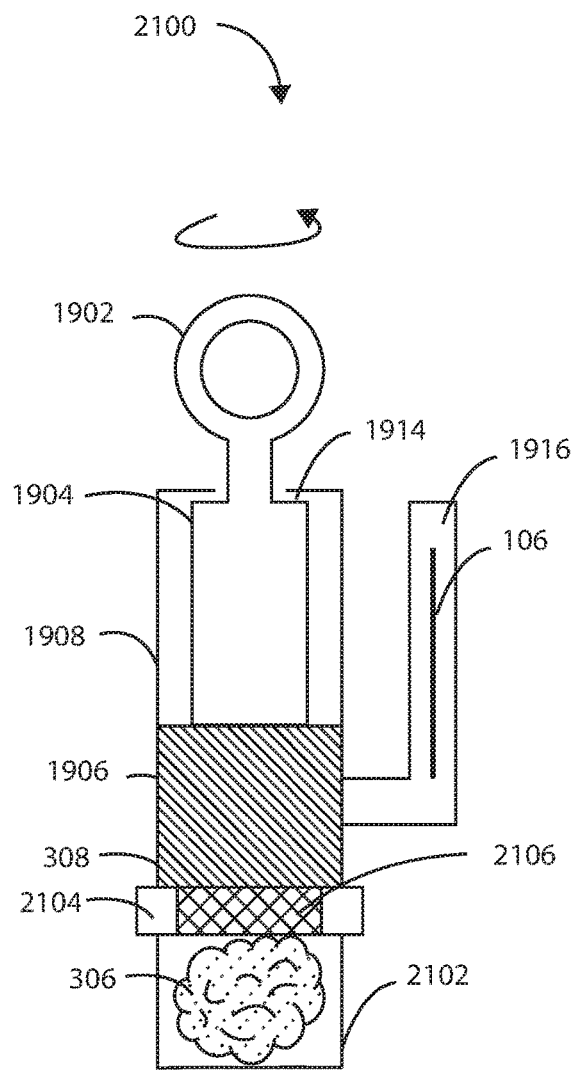
FIG. 21 is a schematic diagram of a container in accordance with various embodiments herein.
Figure 22:
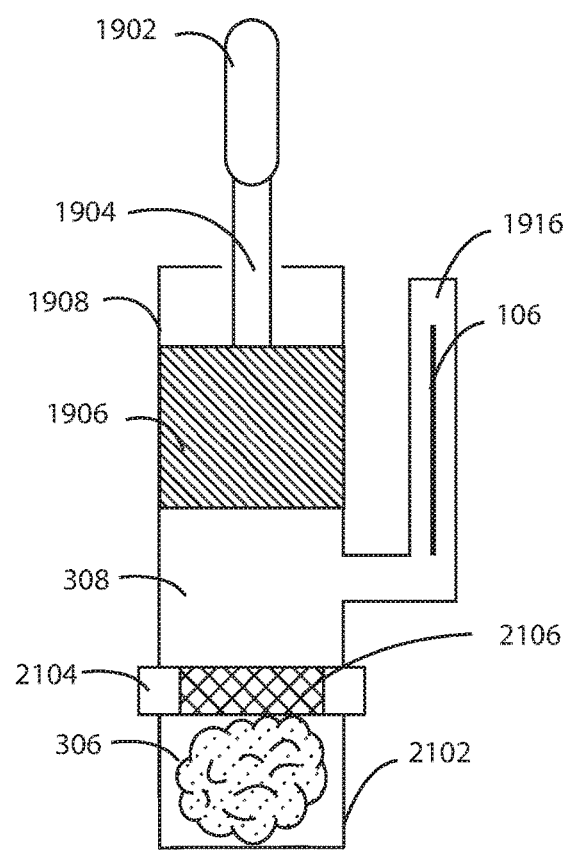
FIG. 22 is a schematic diagram of a container in accordance with various embodiments herein.

The embodiment shown in FIGS. 19 and 20 includes a container 1900 suitable for use to draw in biological samples. It will be appreciated that a similar container can be used for biological samples placed into a separate biological sample cup. Referring now to FIGS. 21 and 22, schematic diagrams of a container 2100 are shown in accordance with various embodiments herein. Container 2100 includes a plunger 1902 having a shaft portion 1904 and a stopper portion 1906. The plunger 1902 can include one or more shoulder portions 1914 that act as a first stop point to prevent plunger travel beyond a predetermined volume. While not shown, plunger 1902 can include additional second, third, fourth, etc. shoulder portions to provide additional stop points. Container 2100 includes a vessel body 1908 that can be removably connected to a biological sample cup 2102. In some embodiments, the biological sample cup 2102 can be removably connected to vessel body 1908 through a cap portion 2104.

Cap portion 2104 can be removably connected to the vessel body 1908 of container 2100 and to biological sample cup 2102. In some embodiments the cap portion 2104 and the vessel body 1908 include complementary threads that are used to secure the cap portion 2104 to the vessel body 1908. Similar complementary threads can be used to secure the biological sample cup 2102 to the cap portion 2104. In some embodiments, the cap portion 2104 can be integral to the biological sample cup 2102 or the vessel body 1908. In other embodiments, the cap portion 2104 can be removably connected to the biological sample cup 2102 or the vessel body 1908. Cap portion 2104 can be configured to be threaded to vessel body 1908 to form an air-tight seal and can be configured to be threaded to biological sample cup 2102 to form an air-tight seal. Cap portion 2104 can include a gas-permeable divider 2106. In some embodiments, gas-permeable divider 2106 can include a mesh, a filter, and the like, provided it allows for the free diffusion of VOCs from the biological sample cup into the vessel body 1908 of container 2100.

The container 2100 can include a sensor element chamber 1916 in fluid communication with the interior of the vessel body 1908 and sealed from an external environment. The sensor element chamber 1916 includes a chemical sensor element 106 disposed within an inert environment. The inert environment within sensor element chamber 1916 can include an inert gas such as nitrogen ($N_2$) gas. In other embodiments, the inert environment within sensor element chamber 1916 can include, but not be limited to, the inert gases helium (He), neon (Ne), argon (Ar), krypton (Kr), or xenon (Xe). The chemical sensor element 106 can include a plurality of discrete graphene varactors as discussed elsewhere herein. In some embodiments, the sensor element chamber 1916 is integral with the vessel body 1908. In other embodiments, the sensor element chamber 1916 is removably attached to the vessel body 1908.

Container 2100 can be used to collect volatile organic compounds (VOCs) that are emitted from a biological sample 306. In other embodiments, the biological sample can include a solid. In some embodiments, the biological sample 306 can include a slurry that contains both a solid or a liquid. In other embodiments, the biological sample can include a liquid. A biological sample 306 can be placed within biological sample cup 2102 and the biological sample cup 2102 can be secured to the vessel body 1908. The stopper portion 1906 of plunger 1902 can be positioned such that it maintains a seal over the sensor element chamber 1916 to block the fluid communication flow path between the vessel body 1908 and the sensor element chamber 1916. The stopper portion 1906 of plunger 1902 can also be in contact with the cap portion 2104 and the gas-permeable divider 2106. In some embodiments, the stopper portion 1906 of plunger 1902 is not in contact with the cap portion 2104 and the gas-permeable divider 2106, leaving a headspace above or around the biological sample 306.

Referring now to FIG. 22, a schematic diagram of a container 2100 with the plunger 1902 in a second configuration is shown in accordance with various embodiments herein. It will be appreciated that plunger 1902 of FIG. 22 is shown rotated 90 degrees with respect to the plunger 1902 of FIG. 22. However, it will be appreciated that the plunger 1902 can be rotated freely from 0 degrees to 360 degrees about its longitudinal axis. Rotation of plunger 1902 can allow plunger 1902 to be pulled further out of the vessel body 1908 beyond a first stop point to an additional stop point. The action of pulling the plunger 1902 further out of the vessel body 1908 creates a vacuum within headspace 308 over biological sample 306. In some embodiments, a counterforce can be applied to plunger 1902 to keep the volume within headspace 308 constant.

The action of pulling the plunger 1902 out of the vessel body 1908 causes a drop in the pressure over the biological sample 306, which provides a driving force for the vaporization of the volatile organic compounds (VOCs) out of the biological sample 306 and into the headspace 308 as gas vapor. Pulling the plunger 1902 out of the vessel body additionally unblocks the fluid communication flow path between the vessel body 1908 and the sensor element chamber 1916, thus exposing the chemical sensor element 106 to a volume of gas within headspace 308, including VOCs.

Disease States

The methods, containers, and systems herein can be used to detect a disease state in a subject. Sample data sets obtained from sensing and storing capacitance of one or more discrete graphene varactors can be used to classify the sample data set into one or more preestablished classifications.

The preestablished classifications can include one or more disease states of a subject. In some embodiments, the disease state can include at least one cancer. The one or more cancers can include, but not be limited to bladder cancer, prostate cancer, breast cancer, pancreatic cancer, ovarian cancer, blood-borne cancer, liver cancer, bile duct cancer, lung cancer, esophageal cancer, thyroid cancer, brain cancer, lymph-borne cancer, colon cancer, or mouth cancer.

The preestablished classifications can also include one or more disease states related to infection by one or more pathogenic bacterial strains. Bacterial strains emit unique sets of VOCs into their environment and can be identified from a subject's biological material based on the difference in emission of VOCs from each. In some embodiments, the bacterial strains can include, but are not to be limited to, bacteria of the genii *Staphylococcus, Streptococcus, Campylobacter, Clostridum, Escherichia, Listeria, Salmonella, Haemophilus, Neisseria, Klebsiella, Pseudomonas, Mycobacterium*, and *Cryptococcus*.

Classification and Pattern Matching

Classifying the sample data set into one or more preestablished disease classifications can be performed according to many different machine learning techniques, such as pattern recognition. Classification can include comparing the sample data set against one or more previously determined patterns using a pattern matching or pattern recognition algorithm to determine the pattern that is the best match, wherein the specific previously determined pattern that is the best match indicates the disease state of the subject.

By way of example, patterns amongst large sets of subject data may be originally identified through machine learning analysis or another similar algorithmic technique. Patterns associated with specific disease state classifications can be derived from labeled "training" data (supervised learning) or in the absence of labeled data (unsupervised learning).

Algorithms for pattern matching used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Classification algorithms can include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms can include categorical mixture models, deep learning methods, hierarchical clustering, K-means clustering, correlation clustering, and kernel principal component analysis. Ensemble learning algorithms can include boosting, bootstrap aggregating, ensemble averaging, and mixture of experts. General algorithms for predicting arbitrarily-structured sets of labels can include Bayesian networks and Markov random fields. Multilinear subspace learning algorithms can include multilinear principal component analysis (MPCA). Real-valued sequence labeling algorithms can include Kalman filters and particle filters. Regression algorithms can include both supervised (such as Gaussian process regression, linear regression, neural networks and deep learning methods) and unsupervised (such as independent component analysis and principal components analysis) approaches. Sequence labeling algorithms can include both supervised (such as conditional random fields, hidden Markov models, maximum entropy Markov models, and recurrent neural networks) and unsupervised (hidden Markov models and dynamic time warping) approaches.

Methods of Treating

Embodiments herein can specifically include methods of treating a disease state in a subject. The method can include obtaining a biological sample from the subject and placing it into a container having a headspace above or around the biological sample. The method can further include contacting a gas from the headspace with a chemical sensor element, the chemical sensor element comprising a plurality of discrete graphene varactors. The method can further include sensing and storing capacitance of the discrete graphene varactors to obtain a sample data set. The method can further include classifying the sample data set into one or more preestablished disease state classifications. The method can further include identifying a therapy to treat the subject based on the disease state classification.

By way of example, one exemplary set of classifications and possible treatments for a disease state are provided below in Table 1.

TABLE 1

| Disease State Classification | Treatment |
| --- | --- |
| No Indication of Disease State | No Treatment |
| Indication of Mild Disease State | Prescription Drug Therapy, OTC Drug Therapy |
| Indication of Severe Disease State | Drug Therapies Including One or More of: antibiotic agent, antineoplastic agent, chemotherapeutic agent Referral for Clinical Therapies Including One or More of: surgical removal of a tumor, mass, or abscess; radiation therapy; chemotherapy; immunotherapy; hormone therapy; ablation therapy; stem cell transplant; photodynamic therapy |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The claims are:

1. A method for detecting a health condition of a subject, comprising:
   obtaining a biological sample from the subject and placing it into a container having a headspace surrounding the biological sample;
   contacting a gas from the headspace with a chemical sensor element, the chemical sensor element comprising one or more discrete graphene varactors, wherein volatile organic compounds (VOCs) from the biological sample that are present in the gas from the headspace interface with the discrete graphene varactors to influence sensed capacitance; and
   sensing and storing capacitance of the discrete graphene varactors to obtain a sample data set,
   wherein obtaining a biological sample comprises obtaining one or more of an organ biopsy, blood, urine, bile, sweat, feces, lymph, cerebrospinal fluid, amniotic fluid, pericardial fluid, peritoneal fluid, saliva, synovial fluid, serous fluid, sebum, bone biopsy, muscle biopsy, cheek swab biopsy, or isolated cells.

2. The method of claim 1, classifying the sample data set into one or more preestablished classifications.

3. The method of claim 2, further comprising identifying a therapy to treat the subject based on the preestablished classification.

4. The method of claim 1, wherein the headspace above or around the biological sample includes a volume of a gas.

5. The method of claim 1, wherein the container is flushed with an inert gas prior to placing the biological sample into the container.

6. The method of claim 1, the container comprising a sample port, wherein the biological sample is placed into the container through the sample port.

7. The method of claim 1, wherein the gas from the headspace is continuously drawn from the container and contacted with the chemical sensor element.

8. The method of claim 1, wherein the biological sample is incubated in the container for a period of time before the gas from the headspace is contacted with a chemical sensor element.

9. The method of claim 1, wherein the biological sample is heated to a temperature in the range of 25 degrees C. to 40 degrees C. prior to contacting the headspace with a chemical sensor element.

10. The method of claim 1, wherein sensing and storing capacitance of the graphene varactors to obtain a sample data set is performed across a range of bias voltages, wherein the range of bias voltages is from −3 V to 3 V.

11. The method of claim 1, further storing additional data regarding the subject beyond sensed capacitance as part of the sample data set that is classified, the additional data comprising at least one of:
   prior disease states of the subject;
   age of the subject;
   results of a physical examination;
   symptoms experienced by the subject; and
   data regarding specific biomarkers of one or more disease states.

12. A method for detecting a health condition of a subject, comprising:
   obtaining a biological sample from the subject and placing it into a container having a headspace surrounding the biological sample;
   heating the biological sample to a temperature in the range of 25 degrees C. to 40 degrees C. prior to contacting the headspace with a chemical sensor element;
   contacting a gas from the headspace with a chemical sensor element, the chemical sensor element comprising one or more discrete graphene varactors, wherein volatile organic compounds (VOCs) from the biological sample that are present in the gas from the headspace interface with the discrete graphene varactors to influence sensed capacitance; and
   sensing and storing capacitance of the discrete graphene varactors to obtain a sample data set,
   wherein the biological sample is heated to a temperature in the range of 25 degrees C. to 40 degrees C. prior to contacting the headspace with a chemical sensor element.

13. The method of claim 12, classifying the sample data set into one or more preestablished classifications.

14. The method of claim 13, further comprising identifying a therapy to treat the subject based on the preestablished classification.

15. The method of claim 12, wherein the biological sample is incubated in the container for a period of time before the gas from the headspace is contacted with a chemical sensor element.

16. The method of claim 12, further storing additional data regarding the subject beyond sensed capacitance as part of the sample data set that is classified, the additional data comprising at least one of:
   prior disease states of the subject;
   age of the subject;
   results of a physical examination;
   symptoms experienced by the subject; and
   data regarding specific biomarkers of one or more disease states.

17. A method for detecting a health condition of a subject, comprising:
   obtaining a biological sample from the subject and placing it into a container having a headspace surrounding the biological sample;
   contacting a gas from the headspace with a chemical sensor element, the chemical sensor element comprising one or more discrete graphene varactors, wherein volatile organic compounds (VOCs) from the biological sample that are present in the gas from the headspace interface with the discrete graphene varactors to influence sensed capacitance;

sensing and storing capacitance of the discrete graphene varactors to obtain a sample data set; and storing additional data regarding the subject beyond sensed capacitance as part of the sample data set that is classified, the additional data comprising at least one of:

prior disease states of the subject;

age of the subject;

results of a physical examination;

symptoms experienced by the subject; and data regarding specific biomarkers of one or more disease states.

18. The method of claim 17, classifying the sample data set into one or more preestablished classifications.

19. The method of claim 18, further comprising identifying a therapy to treat the subject based on the preestablished classification.

20. The method of claim 17, wherein the biological sample is incubated in the container for a period of time before the gas from the headspace is contacted with a chemical sensor element.

* * * * *